(12) United States Patent
Cam et al.

(10) Patent No.: US 12,064,314 B2
(45) Date of Patent: Aug. 20, 2024

(54) DENTAL APPLIANCE COMPLIANCE MONITORING

(71) Applicant: Align Technology, Inc., San Jose, CA (US)

(72) Inventors: Bruce Cam, San Jose, CA (US); Yaser Shanjani, Milpitas, CA (US); Edi Fridman, San Jose, CA (US); Sergey Vinnichenko, Cary, NC (US); Jun Sato, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 90 days.

(21) Appl. No.: 17/448,008

(22) Filed: Sep. 17, 2021

(65) Prior Publication Data

US 2022/0000585 A1 Jan. 6, 2022

Related U.S. Application Data

(63) Continuation of application No. 16/104,781, filed on Aug. 17, 2018, now Pat. No. 11,123,156.

(60) Provisional application No. 62/546,987, filed on Aug. 17, 2017.

(51) Int. Cl.
| | |
|---|---|
| *A61C 19/04* | (2006.01) |
| *A61B 5/00* | (2006.01) |
| *A61C 7/00* | (2006.01) |
| *A61C 7/08* | (2006.01) |

(52) U.S. Cl.
CPC .............. *A61C 7/08* (2013.01); *A61B 5/4833* (2013.01); *A61C 7/002* (2013.01); *A61C 19/04* (2013.01); *A61C 2204/007* (2013.01)

(58) Field of Classification Search
CPC ........ H04B 7/024; H04B 7/0684; A61C 7/08; A61C 7/002; A61C 7/00; A61C 19/04; A61C 19/02; A61C 2204/007; A61C 2204/005; A61C 5/44; A61B 5/4833; A61B 5/48; G06F 2203/04105
USPC .......................................................... 433/24
See application file for complete search history.

(56) References Cited

U.S. PATENT DOCUMENTS

| | | |
|---|---|---|
| 5,820,368 A | 10/1998 | Wolk |
| 6,386,864 B1 | 5/2002 | Kuo |
| 6,783,604 B2 | 8/2004 | Tricca |
| 6,790,035 B2 | 9/2004 | Tricca et al. |
| 6,947,038 B1 | 9/2005 | Anh et al. |
| 7,104,792 B2 | 9/2006 | Taub et al. |
| 7,160,107 B2 | 1/2007 | Kopelman et al. |
| 7,448,514 B2 | 11/2008 | Wen |
| 7,600,999 B2 | 10/2009 | Knopp |
| 7,766,658 B2 | 8/2010 | Tricca et al. |

(Continued)

*Primary Examiner* — Ralph A Lewis
*Assistant Examiner* — Mirayda A Aponte
(74) *Attorney, Agent, or Firm* — Shay Glenn LLP

(57) ABSTRACT

The present disclosure describes devices, systems, and methods for monitoring use of an oral appliance in an oral cavity using extra-oral sensor(s). One method includes sensing one or more physical properties of an oral appliance using an extra-oral sensor, providing a compliance signal from the extra-oral sensor, identifying one or more patient compliance factors based on the compliance signal, the one or more patient compliance factors providing a basis to identify an extent of compliance of usage of the oral appliance with an orthodontic treatment plan, determining the extent of compliance, and outputting the extent of compliance.

23 Claims, 11 Drawing Sheets

(56) References Cited

U.S. PATENT DOCUMENTS

| | | |
|---|---|---|
| 7,771,195 B2 | 8/2010 | Knopp et al. |
| 7,871,269 B2 | 1/2011 | Wu et al. |
| 7,883,334 B2 | 2/2011 | Li et al. |
| 7,914,283 B2 | 3/2011 | Kuo |
| 8,235,715 B2 | 8/2012 | Kuo |
| 8,337,199 B2 | 12/2012 | Wen |
| 8,401,686 B2 | 3/2013 | Moss et al. |
| 8,562,337 B2 | 10/2013 | Kuo et al. |
| 8,684,729 B2 | 4/2014 | Wen |
| 8,758,009 B2 | 6/2014 | Chen et al. |
| 9,119,691 B2 | 9/2015 | Namiranian et al. |
| 9,326,831 B2 | 5/2016 | Cheang |
| 9,655,691 B2 | 5/2017 | Li et al. |
| 9,700,385 B2 | 7/2017 | Webber |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,363,116 B2 | 7/2019 | Boronkay |
| D865,180 S | 10/2019 | Bauer et al. |
| 10,463,452 B2 | 11/2019 | Matov et al. |
| 10,492,888 B2 | 12/2019 | Chen et al. |
| 10,517,701 B2 | 12/2019 | Boronkay |
| 10,537,463 B2 | 1/2020 | Kopelman |
| 10,555,792 B2 | 2/2020 | Kopelman et al. |
| 10,588,776 B2 | 3/2020 | Cam et al. |
| 10,743,964 B2 | 8/2020 | Wu et al. |
| 10,758,323 B2 | 9/2020 | Kopelman |
| 10,781,274 B2 | 9/2020 | Liska et al. |
| 10,881,487 B2 | 1/2021 | Cam et al. |
| 10,912,629 B2 | 2/2021 | Tanugula et al. |
| 11,154,382 B2 | 10/2021 | Kopelman et al. |
| 11,166,788 B2 | 11/2021 | Webber |
| 11,174,338 B2 | 11/2021 | Liska et al. |
| 11,219,506 B2 | 1/2022 | Shanjani et al. |
| 2004/0166462 A1 | 8/2004 | Phan et al. |
| 2005/0014105 A1 | 1/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0199142 A1 | 9/2006 | Liu et al. |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2014/0067334 A1 | 3/2014 | Kuo |
| 2015/0265376 A1 | 9/2015 | Kopelman |
| 2015/0366638 A1 | 12/2015 | Kopelman et al. |
| 2016/0100924 A1* | 4/2016 | Wilson .............. A61C 7/08 206/63.5 |
| 2016/0193014 A1 | 7/2016 | Morton et al. |
| 2016/0242870 A1 | 8/2016 | Matov et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007386 A1 | 1/2017 | Mason et al. |
| 2019/0000592 A1 | 1/2019 | Cam et al. |
| 2019/0000593 A1 | 1/2019 | Cam et al. |
| 2019/0029775 A1 | 1/2019 | Morton et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0343606 A1 | 11/2019 | Wu et al. |
| 2020/0000553 A1 | 1/2020 | Makarenkova et al. |
| 2020/0086553 A1 | 3/2020 | Mojdeh et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0100871 A1 | 4/2020 | Wang et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2021/0078357 A1 | 3/2021 | Venkatasanthanam et al. |
| 2021/0147672 A1 | 5/2021 | Cole et al. |

* cited by examiner

DENTAL APPLIANCE COMPLIANCE MONITORING

CROSS REFERENCE TO RELATED APPLICATIONS

This application is a continuation of U.S. patent application Ser. No. 16/104,781, filed on Aug. 17, 2018, titled "DENTAL APPLIANCE COMPLIANCE MONITORING," now U.S. Pat. No. 11,123,156, which claims benefit of U.S. Provisional Patent Application No. 62/546,987, filed on Aug. 17, 2017, titled "DENTAL APPLIANCE COMPLIANCE MONITORING," each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Dental treatments may involve restorative and/or orthodontic procedures. Restorative procedures may include implanting a dental prosthesis (e.g., a crown, bridge, inlay, onlay, veneer, etc.) intraorally in a patient. Orthodontic procedures may include repositioning misaligned teeth and changing bite configurations for improved cosmetic appearance and/or dental function. Orthodontic repositioning can be accomplished, for example, by applying controlled forces to one or more teeth or a jaw of a patient over a period of time As an example, orthodontic repositioning may be provided through a dental process that uses positioning appliances for realigning teeth. Such appliances may utilize a shell of material having resilient properties, referred to as an "aligner," and/or "orthodontic aligner."

Placement of an aligner over teeth may provide controlled forces in specific locations to gradually move teeth into a new configuration. Repetition of this process with successive appliances in progressive configurations can move the teeth through a series of intermediate arrangements to a final desired arrangement. Aligners can also be used for other dental conditions, such as application of medications, appliances to help with sleep apnea, and other issues.

Some aligner systems utilize a set of aligners that can be used to incrementally reposition teeth without requiring impressions/scans after an initial impression/scan. These aligner systems may use attachments, such as bonded/adhered structures on teeth that interact with active regions of aligners to implement forces on the teeth. The same attachments may be utilized or attachments may be added, removed, or replaced with other attachment shapes that may impart different force characteristics than a previous appliance and attachment combination (i.e., appliance and one or more attachments).

Many treatment plans require patients to wear oral appliances for specified circumstances, such as specified duration(s) or in specified manner(s). While it may be desirable to monitor compliance, it is often difficult to do so. Monitoring compliance may also provide insight into the efficacy of an oral appliance and/or treatment plan is.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The present disclosure describes devices, systems, and methods for monitoring use of an oral appliance in an oral cavity using an extra-oral compliance indicator system in which extra-oral sensor(s) are configured to gather compliance information about the oral appliance while remaining outside the oral cavity.

In the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present disclosure, and should not be taken in a limiting sense.

Figure 1A:
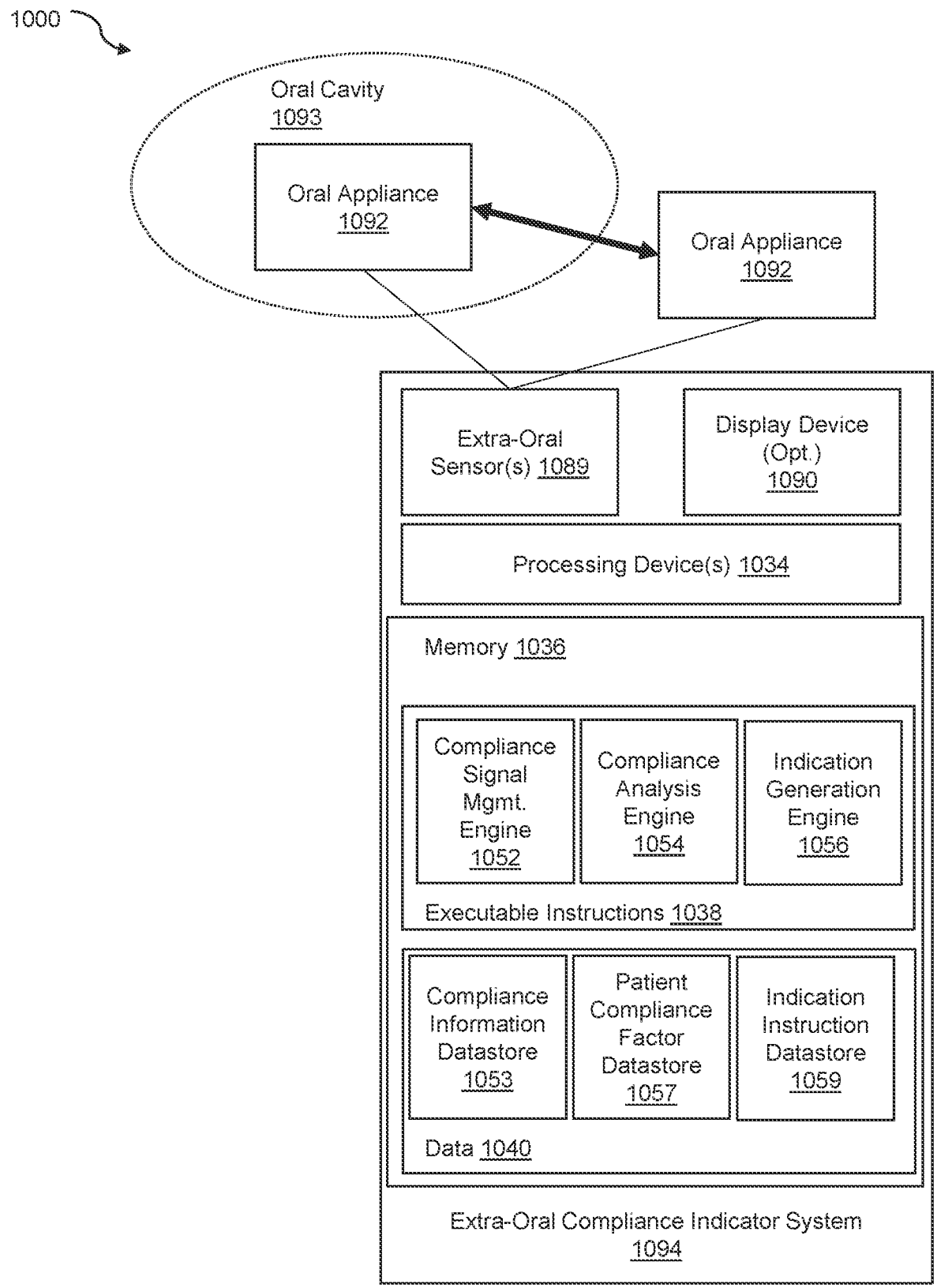
FIG. 1A illustrates an extra-oral compliance monitoring environment for monitoring use of an oral appliance within an oral cavity, according to some implementations of the present disclosure.

FIG. 1A illustrates an extra-oral compliance monitoring environment 100A, according to some implementations. In this example, the extra-oral compliance monitoring environment 100A includes an oral appliance 1092, an oral cavity 1093, an extra-oral compliance indicator system 1094, and a case (not shown in FIG. 1A). One or more of the elements of the extra-oral compliance monitoring environment 100A may be coupled to one another or to modules not explicitly shown.

The oral cavity 1093 may include the oral cavity of a patient. The oral cavity 1093 may correspond to some or all of a patient's mouth. The case (not shown in FIG. 1A) may include a physical container to encase the oral appliance 1092. The case may include a dental appliance packaging box.

The oral appliance 1092 (and any "oral devices" used herein) may include any device used to adjust or maintain teeth and/or skeletal structures within the oral cavity. The oral appliance 1092 may reside in the oral cavity 1093 for various duration(s) and/or under various circumstances. Examples of oral appliances include orthodontic appliances (braces, orthodontic aligners alone or in combination with attachments, etc.), palatal expanders, mandibular modification devices/features, retainers, bruxism devices, etc. As used herein, the language, "dental appliance" and the language, "oral appliance" may be used interchangeably and include a device that implements at least a part of a treatment plan on a patient's teeth and is placed into the patient's oral cavity. In this example, the oral appliance 1092 may reside within the oral cavity 1093 at some times and may reside outside the oral cavity 1093 at other times. The durations of time the oral appliance 1092 resides in the oral cavity 1093 may correspond to times a patient complies with a treatment plan. As an example, some orthodontic treatment plans may require patient's to wear orthodontic appliances for a specified amount of time per day. The oral appliance 1092 may reside within the oral cavity 1093 for time(s) the patient actually complies with the requirements of the orthodontic treatment plan. As patient compliance with a treatment plan may vary, it is noted the durations of time the oral appliance 1092 resides in the oral cavity 1093 may, but need not, correspond with the specifications of a treatment plan.

The extra-oral compliance indicator system 1094 may include extra-oral sensor(s) 1089, a display device 1090, one or more processing devices 1034, and memory 1036. The extra-oral compliance indicator system 1094 and any "extra-oral" device described herein may operate outside the oral cavity 1093. For instance, in some implementations, one or more of the components of the extra-oral compliance indicator system 1094 may not reside on the oral appliance 1092. Some or all of the extra-oral compliance indicator system 1094 may be incorporated into the oral appliance 1092. Some or all of the extra-oral compliance indicator system 1094 may be incorporated extra-orally, e.g., on a case that holds the oral appliance, on extra-oral portions of a patient's body (e.g., portions in a patient's ear), on a computing device such as a mobile phone, tablet, laptop, desktop, etc.

The extra-oral sensor(s) 1089 may comprise a sensor with components that operate outside the oral cavity 1093. The extra-oral sensor(s) 1089 may include physical and/or electrical components that detect or measure one or more physical properties of usage of the oral appliance 1092 and record, indicate, and/or respond to those properties. The extra-oral sensor 1098 may be configured to sense when an oral appliance is inside, or alternatively, outside, a patient's oral cavity. In some implementations, some portions or all of the extra-oral sensor(s) 1089 is incorporated extra-orally. As an example, some portions or all of the extra-oral sensor(s) 1089 may be incorporated into a case configured to hold the oral appliance 1092. As another example, some portions or all of the extra-oral sensor(s) 1089 are incorporated into extra-oral portions of the patient's body, such as portions of the patient's ear. As yet another example, some portions or all of the extra-oral sensor(s) 1089 may be incorporated into a computing device such as a mobile phone, tablet, laptop, desktop, etc. The extra-oral sensor(s) 1089 may be configured to detect whether the oral appliance 1092 is at a specified orientation relative to the oral cavity 1093 (e.g., inside the oral cavity 1093, outside the oral cavity 1093, etc.).

The extra-oral sensor(s) 1089 may be implemented according to a variety of techniques. In some implementations, the extra-oral sensor(s) 1089 comprises an energy source and a discharge circuit that senses discharge of power, energy, current, etc. from the energy source. The discharge circuit may discharge power from a power source through a power draining element when the oral appliance 1092 is at a specified orientation relative to the oral cavity 1093 (e.g., inside the oral cavity 1093, outside the oral cavity 1093, etc.). As one example, the discharge circuit may be configured to implement an open circuit when the oral appliance 1092 is inside the oral cavity 1093 and a closed circuit when the oral appliance 1092 is outside the oral cavity 1093. In such implementations, the energy source may be drained when the oral appliance 1092 is outside the oral cavity 1093. Conversely, the discharge circuit may implement an open circuit when the oral appliance 1092 is outside the oral cavity 1093 and a closed circuit when the oral appliance 1092 is inside the oral cavity 1093, thereby causing the energy source to be drained when the oral appliance 1092 is inside the oral cavity 1093. In various implementations, the extra-oral sensor(s) 1089 comprises a discharge circuit incorporated into a case that is configured to hold the oral appliance 1092.

The extra-oral sensor(s) 1089 may comprise a magnetic sensor that varies a voltage in response to changes in a magnetic field. The changes in the magnetic field may indicate whether the oral appliance 1092 is at a specified orientation relative to the oral cavity 1093. The magnetic sensor may use the Hall effect (e.g., the production of a potential difference across an electrical conductor when a magnetic field is applied in a direction perpendicular to that of the flow of current) in order to sense changes to a magnetic field. In some implementations, a first portion of the magnetic sensor is incorporated into the oral appliance 1092 and a second portion of the magnetic sensor is located outside the oral cavity 1093. As examples, the first portion of the magnetic sensor may comprise a magnetic and/or metallic portion of the oral appliance 1092. The second portion of the magnetic sensor may be incorporated outside the oral cavity 1093, e.g., in a patient's ear, nose, throat, and/or on jewelry or other items that can be attached to the patient.

In some implementations, the extra-oral sensor(s) 1089 comprises a metallic sensor that senses when the oral appliance 1092 is inside its case. In some implementations, a first portion of the metallic sensor is incorporated into the oral appliance 1092 and a second portion of the metallic sensor is incorporated into the case. In such implementations, the metallic sensor may be configured to sense proximity, conductive characteristics, or other characteristics of the oral appliance 1092.

In various implementations, the extra-oral sensor(s) 1089 may comprise a biosensor that senses living organism(s), biological molecule(s) (e.g., especially enzymes, antibodies, etc.), etc. to detect the presence of specific chemicals on the oral appliance 1092. Such chemicals may be included, even residually, on saliva or other biological materials on the oral appliance 1092 after the oral appliance 1092 has been removed from the oral cavity 1093.

The extra-oral sensor(s) 1089 may include one or more image sensors that are configured to use image recognition techniques to determine whether or not the oral appliance 1092 is proximate to it and/or within the case of the oral appliance 1092. The extra-oral sensor(s) 1089 may, for instance, comprise a light source sensor incorporated into the case. The light source sensor may comprise a light source and a light detector that determines when the light source has been blocked. As noted herein, the light source may be blocked when the oral appliance 1092 is inside its case; the detector may provide information corresponding to detection of the oral appliance 1092 accordingly. Alternatively, the light source may be blocked when the oral appliance is outside its case; the detector may correspondingly provide information corresponding to detection of the oral appliance 1092.

The extra-oral sensor(s) 1089 may include image sensor(s) that detect features of the oral appliance 1092. As such, the extra-oral sensor(s) 1089 may implement cameras and/or other image capture devices that allow images of the oral appliance 1092 to be captured. The cameras and/or image capture devices may be used to compare depictions of the oral appliance 1092 with depictions of known or estimated properties (shapes, sizes, use properties, thicknesses, stages, etc.) of the oral appliance 1092. The cameras and/or image capture devise may be used to compare locations and/or other metadata of depictions of the oral appliance 1092 to see, e.g., if the oral appliance 1092 is at known location.

As another example, the extra-oral sensor(s) 1089 may comprise one or more locational sensors that sense locations of the oral appliance 1092. The extra-oral sensor(s) 1089 may include, e.g., sensors using Bluetooth, near field communication (NFC), Ultraband, and Zigbee, among other communication types, or longer range (greater than 15 meters), such as infrared or Wi-Fi communication types.

As yet another example, the extra-oral sensor(s) 1089 may include sensors configured to detect material properties of the oral appliance 1092 based on a response to a light source (e.g., infrared light source). For instance, the extra-oral sensor(s) 1089 may be configured to identify reflective, refractory, diffusive, etc. patterns from light shined on the oral appliance 1092. In some implementations, the extra-oral sensor(s) 1089 may be part of a system to detect whether the materials used to form the oral appliance 1092 are of a specific polymeric material or are counterfeits, fakes, etc.

The extra-oral sensor(s) 1089 may be configured to provide a compliance signal that indicates whether or not the oral appliance is inside/outside the patient's oral cavity. The compliance signal may be used to determine compliance information. "Compliance information," as used herein, may include any information related to patient compliance with a treatment plan, and can include such factors as time(s) an oral appliance has been worn and/or in an oral cavity, time(s) an oral appliance has not been worn and/or in an oral cavity, physical modification (e.g., of shapes, sizes, material properties, etc.) of an oral appliance as a result of wear and/or residence in/out of an oral cavity, etc. In various implementations, the compliance information may be used to determine whether or not a patient is sufficiently complying with parameters of a treatment plan. The compliance information may, for instance, be used to determine whether or not a patient is wearing oral appliance(s) for prescribed periods of time. The compliance information may also be used as the basis of one or more display elements that display to the patient and/or treatment professionals the extent a patient is complying with parameters of a treatment plan.

The display device 1090 may include a physical device configured to display data. The display device 1090 may include a computer screen, video and/or graphics hardware, a touchscreen, etc. In some implementations, the display device 1090 includes a light, e.g., a Light Emitting Diode (LED) that provides an indicator to a user. The display device 1090 may be configured to display the data to a patient, to a treatment professional, etc.

The processing device(s) 1034 may include one or more physical computer processors that can execute computer-program instructions and/or computer-implemented methods. The processing device(s) 1034 may execute the executable instructions 1038 in the memory 1036. The memory 1036 may include volatile and/or non-volatile memory. The memory 1036 may include executable instructions 1038 and data 1040.

The executable instructions 1038 may include a compliance signal management engine 1052, a compliance analysis engine 1054, and an indication generation engine 1056. As used herein, an engine may include computer-program instructions executed by one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like.

As such, a first engine and a second engine can be executed by one or more dedicated processors or a first engine and a second engine can share one or more processors with one another or other engines. Depending upon implementation-specific or other considerations, an engine can be centralized or its functionality distributed. An engine can be executed by hardware, firmware, or software embodied in computer-readable medium for execution by the processor(s). The processing device(s) 1034 may transform data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices and need not be restricted to only one computing device. In some embodiments, the cloud-based engines can execute functionalities and/or modules that end users access through a web browser or container application without having the functionalities and/or modules installed locally on the end-users' computing devices.

The compliance signal management engine 1052 may implement one or more automated agents configured to process a compliance signal from the extra-oral sensor 1089. The compliance signal management engine 1052 may receive the compliance signal over a computer-readable medium coupling the extra-oral sensor 1089 to it. The compliance signal may be relevant to compliance information, as noted further herein. In some implementations, the compliance signal management engine 1052 is configured to extract and/or provide compliance information to other modules, such as the compliance analysis engine 1052.

The compliance analysis engine 1054 may implement one or more automated agents configured to analyze patient compliance with an orthodontic treatment plan based on the compliance information. In some implementations, the compliance analysis engine 1054 may implement rules to identify patient compliance factors based on compliance information. "Patient compliance factors," as used herein, may include factors that indicate whether or not a patient usage of the oral appliance 1092 complies with a treatment plan. Patient compliance factors may include whether time(s), date(s), material properties, etc. of usage correspond with usage typically found for a treatment plan. As an example, if a treatment plan calls for the oral appliance 1092 to be worn a specified amount of time in a day, the compliance analysis engine 1054 may determine whether compliance information indicates wear for the specified amount of time.

The indication generation engine 1056 may implement one or more automated agents configured to provide a compliance indicator based on patient compliance factors. A "compliance indicator," as used herein, may include an indication of the extent a patient is complying with a treatment plan that calls for use of the oral appliance 1092. Compliance indicators may include a determination of whether or not a patient is complying with parameters of a treatment plan. In various implementations, the compliance analysis engine 1054 may represent the compliance indicator as a Boolean value, other numerical score representing compliance, an alphanumeric sequence representing compliance, etc. In some implementations, the indication generation engine 1056 instructs the display device 1090 to display compliance indicators.

The memory 1040 may include a compliance information datastore 1053, a patient compliance factor datastore 1057, and an indication instruction datastore 1059.

As used herein, datastores may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud based datastore is a datastore that is compatible with cloud-based computing systems and engines.

The compliance information datastore 1053 may be configured to store compliance information. The patient compliance factor datastore 1057 may be configured to store patient compliance factors. The indication instruction datastore 1059 may be configured to store compliance indicators.

In some implementations, the devices of the extra-oral compliance monitoring environment 100A may operate to monitor patient compliance with an orthodontic treatment plan, which is discussed further herein. As noted herein, depending on the implementation, the extra-oral sensor(s) 1089 may, through communication and/or sensing of the oral appliance 1092, determine whether or not the oral appliance 1092 resides within the oral cavity 1093. The extra-oral sensor(s) 1089 may provide to the compliance signal management engine 1052 a compliance signal which may contain therein compliance information representative of compliance to an orthodontic treatment plan. The compliance signal management engine 1052 may operate to process the compliance signal from the extra-oral sensor 1089 and provide it to the compliance analysis engine 1054, which may operate to identify patient compliance factors based on the compliance information. In various implementations, the indication generation engine 1056 may operate to provide a compliance indicator based on the patient compliance factors. The indication generation engine 1056 may further configure the display device 1090 to display a representation of the compliance indicator.

Figure 1B:
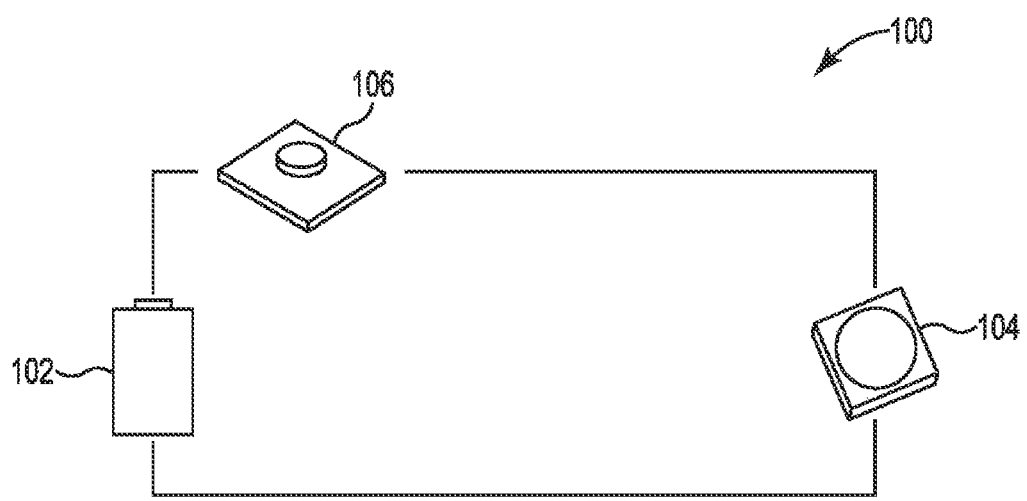
FIG. 1B illustrates a circuit diagram of a compliance monitoring device according to a number of embodiments of the present disclosure.

FIG. 1B illustrates a diagram of a compliance monitoring circuit 100 according to some embodiments. The compliance monitoring circuit 100 may correspond to portions of the extra-oral sensor(s) 1089 shown in FIG. 1A. More particularly, the compliance monitoring circuit 100 may implement a discharge circuit that discharges power from a power source 102 through a power draining element 104 when a circuit actuation mechanism 106 has indicated the oral appliance 1092 is (depending on implementation) either inside or outside the oral cavity 1093. The compliance monitoring circuit 100 may be incorporated into and/or coupled to the compliance signal management engine 1052 and/or the oral appliance 1092 (shown in FIG. 1A). In some embodiments of the present disclosure, an oral appliance compliance system can include an oral appliance having a body. The oral appliance can also include a power source attached to the body, wherein the power source has a predetermined power level and a power draining element and a compliance component attached to the body, the compliance component connected to the power source, wherein a comparison of the predetermined power level and a power level of the power source after interaction with the power draining element is used to indicate whether the patient is wearing the oral appliance in compliance with an amount of time provided in a treatment plan created for the patient.

The compliance component can include a power source having a predetermined power level and a power draining element, wherein a comparison of the predetermined power level and a power level of the power source after interaction with the power draining element is used to indicate whether the patient is wearing the oral appliance in compliance with an amount of time provided in a treatment plan created for the patient, the compliance component including a sensor to indicate whether the oral appliance is out of a patient's mouth. FIG. 1B illustrates one such system.

FIG. 1B illustrates a circuit diagram of a compliance monitoring device according to a number of embodiments of the present disclosure. In the embodiment of FIG. 1B, the compliance monitoring circuit 100 has the power source (e.g., battery or other type of power cell) 102, a capacitor (not shown in FIG. 1B), the power draining element 104, and the circuit actuation mechanism 106. This design can be configured in two ways. Specifically, the device can have a first configuration wherein the device is actuated when the patient is wearing the device and a second configuration wherein the device is actuated when the patient is not wearing the device.

In the first configuration, the circuit actuation mechanism 106 can be actuated when the oral appliance is being worn. For example, the circuit actuation mechanism can be a button that when depressed, allows power to flow through the circuit to the power draining element which thereby reduces the power in the power source over time. If the amount of power (a starting power level) is known at the beginning of treatment and the amount of power that is drained from the circuit over time is also known, then the amount of time that the oral appliance is worn can be calculated based upon the comparison of the power level before treatment commences and the power level after the treatment period has ended.

In the second configuration, the circuit actuation mechanism 106 can be actuated when the oral appliance is not being worn. For example, the circuit actuation mechanism can be a button that when not depressed, allows power to flow through the circuit to the power draining element which thereby reduces the power in the power source over time. As with the first configuration, if the amount of power (a starting power level) is known at the beginning of treatment and the amount of power that is drained from the circuit over time is also known, then the amount of time that the oral appliance is worn can be calculated based upon the comparison of the power level before treatment commences and the power level after the treatment period has ended.

This second configuration may need less power, in comparison to the power needed for the first configuration, available in the power source (and, therefore, potentially a smaller power source) as the patient should be wearing the oral appliance a substantial majority of the time during the treatment period. For example, some treatment plans recommend that a patient wear their dental appliance eighteen hours out of a twenty-four hour period. Accordingly, the circuit of the first configuration would be actuated and draining power for eighteen hours out of a twenty-four hour period for each day over the period of treatment. As this configuration tracks the actual time that the oral appliance is in the mouth of the patient, it may be beneficial in some implementations.

The circuit of the second configuration alternatively tracks the time the oral appliance is not in the mouth of the patient. Such a configuration would be actuated and draining power for six hours out of a twenty-four hour period for each day over the period of treatment. As can be determined by this analysis, the power source could accordingly, be reduced by two thirds the capacity of the first configuration, which could be a substantial savings in form factor, amount of power, cost, and comfort of the patient and could offer more options with regard to placement of the power source and/or the compliance monitoring device as a whole, among other benefits.

The compliance monitoring device can be configured to track the total time of use of the oral appliance or non-use of the oral appliance or can be set to track compliance to a threshold. For example, as discussed above, if the starting power level (e.g., voltage) is known and the power source can be drained in a metered manner to a lower power level that is above zero, then the difference in power levels can be compared and the time of compliance can be calculated based upon the power used and the known level of substantially uniform draining of the power source over time.

However, if a treatment professional simply wants to know whether the oral appliance was worn for a threshold amount of time, the initial power level can be selected such that compliance is achieved when the power source is fully depleted (power level is zero). In this manner, a smaller power source may be used and less power may be needed.

Such an embodiment could also be used to provide the amount of compliance below the threshold. For example, a similar calculation could be done with respect to that above regarding ending power levels above zero (e.g., (initial power level minus ending power level above zero)/drainage rate=amount of compliance).

The circuit 100 is preferably of a form factor sufficiently small to be attached to an oral appliance and not be noticeable to the patient wearing of the appliance with regard to the comfort of the patient. For example, a preferable embodiment would be sized such that it can be substantially embedded (as will be discussed in more detail below) and not change the exterior shape of the oral appliance.

In some embodiments, the form factor of the compliance monitoring device being attached and/or embedded within the oral appliance may change the exterior shape of the oral appliance up to 2 mm in each of one or more dimensions without substantially affecting the patient's comfort. Accordingly, such embodiments and perhaps others with even larger changes would be acceptable to the patient and, as such, are suitable embodiments of the present disclosure.

In some embodiments, the power source may be located remotely from one or more of the other components of the circuit. For example, an oral appliance may have surfaces that form separate cavities for the placement of each tooth along one jaw of the patient and the power source may be positioned on a first surface forming a cavity of a first tooth while the other components are positioned on a second surface forming a cavity of a second tooth. In some embodiments, the power source may be on a lingual surface of a cavity of a tooth and the one or more other components may be on a buccal surface of the cavity of the same tooth.

The power source 102 is preferably of a small form factor and, as discussed above, has sufficient power to allow the compliance device to function over the course of the length of the treatment period in which the patient is to be using the oral appliance (e.g., a week, a month, a year, etc.) upon which the compliance monitoring device is to be worn. For example, in some embodiments, if the oral appliance is supposed to be used by the patient for two weeks, the power source should last slightly longer than two weeks, such that the power source is not fully exhausted before the end of the treatment period.

Further, in some embodiments, compliance can be checked during treatment by comparing a pretreatment power level with a current power level. Once the difference is calculated the resultant power level can be compared to an amount of compliance based on the power drain rate for the time period the treatment has been on going to see if compliance is being achieved. This can be helpful during a treatment period to correct dental appliance usage before a full treatment period has gone by, among other benefits.

In some embodiments, the power source can be rechargeable to enable the oral appliance to be reused. For example, the oral appliance can be a retainer and the power source can have sufficient power to measure compliance between visits to the treatment professional. The power source can then be recharged with sufficient power to track compliance between the present visit and the next visit.

In some embodiments, the amount of recharge power can be different for times between visits that are different lengths, such as six months between visits and three months between visits. For example, is some embodiments, a first patient may have regular visits every three months and a second patient may have visits every six months.

In such embodiments, the treatment professional may fill the power supplies to different levels and/or the power supplies may be of different sizes. In some embodiments, a single patient may have a period of six months between visits and another period of three months between visits. In such an embodiment, the treatment professional could fill the power source to different levels or, in some embodiments, the treatment professional could install a larger or smaller power source to accommodate the different time period.

The power draining element can be any resistive element that will drain power at a known metered rate over time. One suitable element is a light source such as a light emitting diode (LED). Light emitting diodes can be beneficial as they are relatively inexpensive, among other benefits.

In such an embodiment, a compliance determination device can be used to measure a characteristic of emitted light from the light source and determine whether a user of the oral appliance is in compliance based on the characteristic of the emitted light. Suitable examples of characteristics that can be measured can be luminosity, intensity, wavelength, and any other characteristic that can change as a power supply providing power to a light source loses power over time.

Another suitable element is a clock circuit. For example, a clock circuit can be provided that records the time when it stops. If the start time is known, then the time of compliance can be calculated based on the difference between the start and stop times. If the clock records the time it stops, this computation can be done at any time after it stops and therefore can be beneficial in some implementations, as it does not need to be calculated right away or before the power source is exhausted, among other benefits.

The circuit actuation mechanism can be any suitable actuation mechanism. For instance, a pressure sensitive actuation mechanism can be used to activate the sensor. In such an implementation, the pressure sensitive actuation mechanism can be used to activate the sensor when the pressure sensitive actuation mechanism is placed against a surface of a tooth of the patient. This mechanism can be used to either actuate the circuit or disable the circuit depending on whether the circuit is designed to track time that the appliance is in use or not in use.

For example, as discussed above, a button type mechanism that actuates the circuit either when it is depressed or not depressed can be a suitable type of circuit actuation mechanism. Other suitable types of actuation mechanisms can be a proximity mechanism, where the mechanism senses proximity to a tooth, a chemical sensor where the sensor determines contact with a chemical in the air or saliva in the mouth of the patient, or a wetness sensor wherein the sensor determines contact with saliva. In each of these examples, the detection of the sensed item can either be used to actuate the circuit or turn off the circuit depending on whether the circuit is being used to monitor the time the oral appliance is in the mouth of the patient or out of the mouth of the patient.

In some embodiments, as shown in FIG. 1B, the system can include the circuit 100, having a power source (e.g., battery or other type of power cell) 102, a power draining element 104, and a circuit actuation mechanism 106 (e.g., to sense whether the oral appliance is out of a patient's mouth). In such an embodiment, the power draining element would be continuously draining the power source when the circuit actuation mechanism is activated. Such an embodiment may be beneficial, for example, in reducing the complexity of the system, assembly time, parts costs, among other benefits.

However, in some embodiments, a resistor-capacitor (RC) circuit can be used in the system. Such a circuit, when, for example, used with an LED or other light source, causes the light to blink.

In this manner, the light can be used to monitor compliance, but it is not on all the time when actuated and thereby less power needs to be provided by the power source. This allows less power to be added to the power source and/or a smaller power source to be used.

Some embodiments can include a transmitter to transmit compliance data from the compliance component to a remote device. In various embodiments, compliance data can be power level data or clock circuit data such as a number of total clock cycles and/or cycles since the last time a transmission of such data was sent.

A compliance component can, for example, analyze a power level of the power source and determine whether a user of the oral appliance is in compliance based on the power level indicated as compared to a pretreatment power level or based on a predetermined threshold power level that has been determined, for example, through testing of the circuit. This, for instance, can be accomplished when a compliance determination device is connected to the power source, analyzes a power level of the power source, and determines whether a user of the oral appliance is in compliance.

Figure 2:
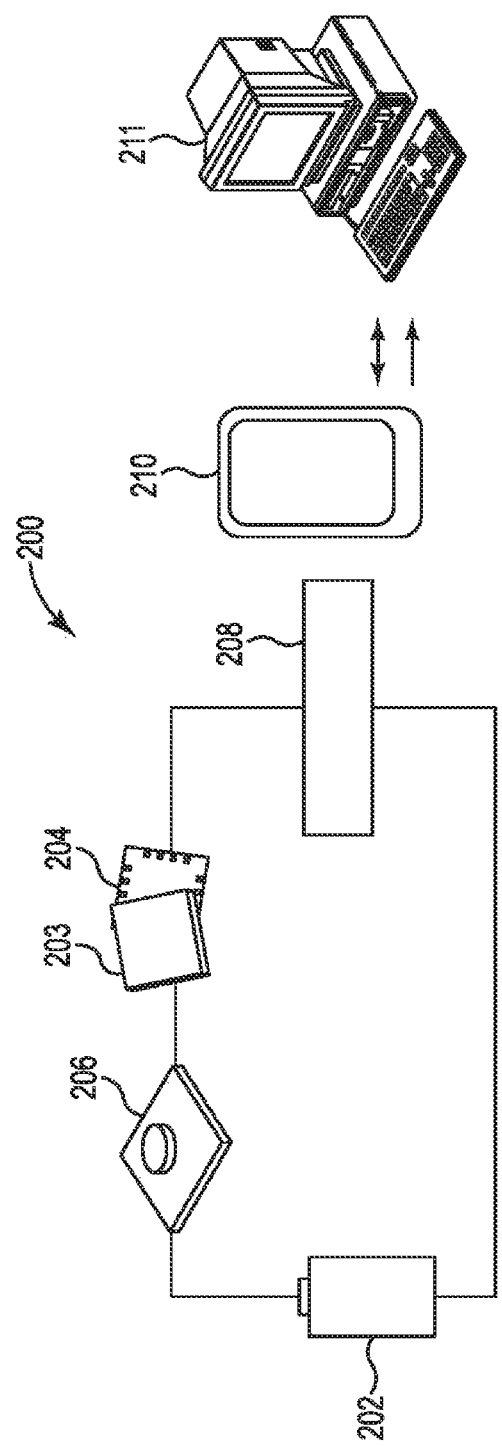
FIG. 2 illustrates a circuit diagram of another compliance monitoring device according to a number of embodiments of the present disclosure.

As discussed in more detail in FIG. 2, in some embodiments, the oral appliance compliance system can include a compliance determination device that receives the compliance data (in a wired or wireless communication) and determines whether a user of the oral appliance is in compliance with a defined threshold of usage for a treatment period based on a comparison of the compliance data received and a threshold value. As discussed herein a threshold value could be a continuous period, such as three hours in the case in one day (24 hour period), or a cumulative period, such as 25 hours during an entire treatment period. The threshold can be any suitable threshold and can be determined and set, for example, by the manufacturer of the circuit or case, by the treatment professional, or by the patient or their parent or guardian, in various embodiments.

The compliance determination device could, in some implementations be used to provide power to the power source in a wired or wireless manner. This could be accomplished by having a power scavenging component as part of the circuit to collect energy from the compliance determination device and use the collected energy to increase the amount of power stored by the power source. This can, for example, be accomplished via near field communication (NFC) technology that can be used to transfer energy from a device that comes within the range of a near field antenna. Movement, temperature, light, or other power sources used to provide power can be used with scavenging technologies to provide power to the power source connected to the compliance component.

Additionally, any power scavenging technology can be used to provide power to the power source connected to the compliance component. Further, although described in some areas of this disclosure as having power provided from the compliance determination device, it should be noted that any device can be used to provide power to the power source connected to the compliance component.

As described above, in some embodiments, an oral appliance compliance system can include a compliance component to be attached to a body of an oral appliance that has a power source with a predetermined power level and a power draining element. In such an embodiment, a comparison of the predetermined power level and a power level of the power source after interaction with the power draining element can be used to indicate whether the patient is wearing the oral appliance in compliance with an amount of time provided in a treatment plan created for the patient. In this manner, compliance can be measured without having a sensor as part of the circuit on the body of the oral appliance. Such an implementation reduces the amount of components used and could reduce the form factor of the compliance component, which has several benefits, as discussed above.

In another embodiment, an oral appliance compliance system includes a compliance component attached to a body of an oral appliance to be positioned in the mouth of a patient that has a power source with a predetermined power level and a power draining element. A power sensor can be used to determine the predetermined power level. For example, this can be accomplished through use of a voltage measuring device connected to the compliance component and measured at manufacture, packaging of the oral appliance, presentation to the patient by a treatment professional, or other suitable time. Additionally, a power sensor can measure the power level of the power source after interaction with the power draining element to determine values to compare the predetermined value with the after interaction value.

The comparison of the predetermined power level and a power level of the power source after interaction with the power draining element can be used to indicate whether the patient is wearing the oral appliance in compliance with an amount of time provided in a treatment plan created for the patient. The compliance component also can include a power source and a sensor to indicate whether the patient is wearing the oral appliance in compliance with an amount of time provided in a treatment plan created for the patient.

In such an embodiment, the sensor can, for example, be a clock circuit that counts elapsed time since a last reading. The sensor can, for example, be activated when the appliance is removed from the mouth of the patient.

FIG. 2 illustrates a circuit diagram of a compliance monitoring circuit 200 according to a number of embodiments of the present disclosure. The embodiment of FIG. 2 is similar to FIG. 1B in that the circuit 200 tracks the depletion of the power source 202 over time by a power draining element 203. The compliance monitoring circuit 200 may correspond to portions of the extra-oral sensor(s) 1089 shown in FIG. 1A. More particularly, the compliance monitoring circuit 200 may implement a discharge circuit that discharges power from a power source 202 through a power draining element 204 when a circuit actuation mechanism 206 has indicated the oral appliance 1092 is (depending on implementation) either inside or outside the oral cavity 1093. The compliance monitoring circuit 200 may be incorporated into and/or coupled to the compliance signal management engine 1052 and/or the oral appliance 1092 (shown in FIG. 1A). As an example, at least parts of a transmission component 208, a remote device 210, and/or another remote device 211 may be incorporated into the extra-oral compliance indicator system 1094, shown in FIG. 1A.

In the embodiment of FIG. 2, however, the circuit also includes a transmission component 208 that can transmit current compliance information to a remote device 210. The transmission component can be any suitable transmitter. The circuit can also include an integrated circuit 204, as is described herein. In some embodiments, the transmission component can be an antenna and the transmitter can either be part of the transmission component 208 or part of the integrated circuit 204.

For example, in some embodiments, it would be beneficial to use a small form factor to minimize any potential change in the form factor of the oral appliance. Additionally, in some embodiments, the transmission component can be placed at a location that is on the body of the oral appliance but not near the power source and/or other components of the circuit. The transmission component can be used to send information, via a wireless or wired connection, to a device that is not on the oral appliance.

As with other wireless communication elements described herein, the communication type can be either short range (up to 15 meters), such as Bluetooth, near field communication, Ultraband, and Zigbee, among other communication types, or longer range (greater than 15 meters), such as infrared or Wi-Fi communication types. As is commonly understood, longer range communication types can be used in short range applications, but short range communications types cannot be used for longer range applications that require distances longer than their maximum range.

As indicated in FIG. 2 by the arrows next to remote device 210, in some embodiments, short range communication (e.g., Bluetooth) can be used to communicate the compliance information to the remote device 210 and short or long range communication (e.g., Wi-Fi) can be used to communicate the information to another remote device 211, such as a desktop or portable computing device or to an output device, such as a printer or memory device. Such an implementation can be beneficial, for example, where the compliance information can be taken at a dentist's chair and its location is not within short range communication of the transmission component. This can allow for the use of a short range transmission component, which typically have a smaller form factor, less expensive, and use less power than longer range components.

In such embodiments, the compliance system 200 may also include a processor or other logic type circuitry to process the collecting, storage, and sending of the compliance information. Examples of a computing system and memory layout that may be suitable for use with embodiments of the present disclosure are provided in FIGS. 6 and 7 below. In some embodiments, the processor can also analyze the compliance data received and provide a compliance determination that can be sent to the remote device. Memory can also be provided to store the data or other compliance information (e.g., compliance determination). The processor/logic and memory can be provided by separate components, or can be provided by an integrated circuit, such as element 204 of FIG. 2.

As discussed, some embodiments may use a processor and memory or logic to perform various functions. Memory can be coupled to processor or logic circuit. The memory can be volatile or nonvolatile memory. Memory can also be removable (e.g., portable) memory, or non-removable (e.g., internal) memory. For example, memory 108 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disk read-only memory (CD-ROM)), flash memory, a laser disk, a digital versatile disk (DVD) or other optical disk storage, and/or a magnetic medium such as magnetic cassettes, tapes, or disks, among other types of memory.

Memory can also be located internal to another remote device (e.g., enabling data or computer readable instructions to be uploaded or downloaded over the Internet or another wired or wireless connection). Memory can also store executable instructions, such as, for example, computer readable instructions (e.g., software), for providing the functionalities described and executed by the processor according one or more embodiments of the present disclosure.

A processor can be any suitable computing device processor for accomplishing the functions described herein. Logic can be provided by an integrated circuit and can be used in place of a processor (and in some cases, memory) to provide the functionalities described herein.

Remote devices can be various devices capable performing the functions of a remote device in accordance with embodiments of the present disclosure (e.g., a desktop computer, laptop computer, tablet, smart phone, and/or personal digital assistant (PDAs), for instance, among others).

In some embodiments, the remote device includes a display. In some embodiments, the display can be a portion of a device separate from the remote device and may be alternatively referred to as a display device. Display 104 can be a graphic user interface (GUI) that can provide (e.g., display and/or present) and/or receive information (e.g., data and/or images) to and/or from a user. For example, display can include a screen that can provide information to a user and/or receive information entered into display by the user. However, embodiments of the present disclosure are not limited to a particular type of display.

Figure 3:
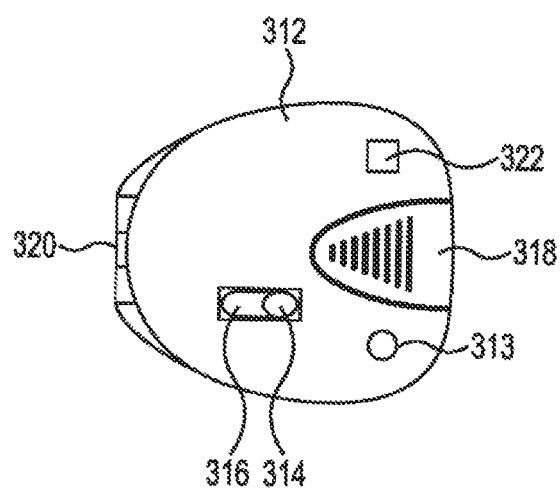
FIG. 3 illustrates a front view of a storage case for an oral appliance according to a number of embodiments of the present disclosure.

FIG. 3 illustrates a front view of a storage case for an oral appliance according to a number of embodiments of the present disclosure. The embodiment shown in FIG. 3 is another type of compliance system that can be used to determine whether a patient is complying with their treatment plan with regard to the amount of time they are supposed to be wearing their dental appliance. The storage case may incorporate one or more portions of the extra-oral compliance indication system 1094, shown in FIG. 1A.

In the embodiment of FIG. 3, the oral appliance compliance system includes an oral appliance storage case wherein an oral appliance is to be placed when not in the mouth of a patient. The storage case includes a compliance component attached to a body 312 of the storage case. The compliance component includes a power source 322 and a sensor to indicate whether the patient is not storing the device for a period over a threshold period of time.

The sensor can be any suitable sensing mechanism that allows the tracking of the time that the oral appliance is within the storage case. In the embodiment illustrated in FIG. 3, the sensor is a switch mechanism having a slider 314 located within a slot 316 that closes a circuit attached to the power source. The circuit can be similar to those described in FIGS. 1 and 2 or could be a circuit having the power supply, a clock circuit, and the switch mechanism.

In some embodiments, the sensor includes a patient actuated sensor to indicate at least one of the placement into and the removal from the storage case of the appliance. For example, as shown in the embodiment of FIG. 3, the patient places the switch in the "on" position when the patient places their dental appliance in the storage case, thereby activating the circuit. When they remove the oral appliance from the storage case, they place the switch in the "off" position and the circuit is deactivated.

In some embodiments, the threshold period of time represents the maximum amount of time that a patient can have the appliance out of their mouth during a particular treatment period. This would indicate that the oral appliance has been in the mouth for the minimum amount of time as prescribed by the patient's treatment plan and therefore, the patient is in compliance.

The threshold period of time for storing the oral appliance can be any suitable amount of time determined by a treatment professional. This time can be set, for example, by the treatment professional and can be kept on a remote computing device (mobile device such as a phone, tablet, or laptop or a desktop computing device, accessed via a wired or wireless connection) that is used to determine whether compliance is met once data from the circuit is received. This time period can be a standard time period for a particular stage of a treatment plan (e.g., stage 2's threshold is 240 hours over wear over a two week period regardless of the patient) or can be determined by the treatment professional and provided to the computing device once the treatment plan has been created by the treatment professional. A treatment plan as used herein can describe plans having just one period of treatment (e.g., when describing a period of use for some types of mandibular adjustment devices, some devices for addressing a malocclusion, such as overjet or overbite, a bruxism device, some types of retainers, etc.) or can describe plans having multiple stages of treatment each having a period of treatment (e.g., when describing a period of use for some types of mandibular adjustment devices, some devices for addressing a malocclusion, such as overjet or overbite, treatment for aligning teeth using aligners, etc.).

In some embodiments, rather than having a switch mechanism, the sensor is activated by the closure of the storage case. For example, the sensor can be activated by a mechanism on the latch 318 of the storage case 312 wherein closure of the storage case and securing of the latch closes the circuit, thereby activating the sensor. In some embodiments, the securing of the latch can open the circuit.

Alternatively, the actuation mechanism can be associated with the hinge 320 of the storage case. For example, the sensor can be activated by a mechanism on the hinge 320 of the storage case 318 wherein closure of the storage case and positioning the hinge in a closed position closes the circuit, thereby activating the sensor. In some embodiments, the positioning of the hinge in a closed position can open the circuit.

Some such devices can also activate an alarm on or in the case if the oral device has been in the case for greater than a threshold time period. The time period can, for example, be a continuous time that the oral device is in the case (e.g., more than three consecutive hours in the case) or can be a cumulative time period that is made up of several non-continuous time periods that are accumulated over a treatment period (e.g., a few hours each 24 hour day). The time period threshold can be determined and set, for example, in the hardware or software of the case, during manufacture, after manufacture, set by the treatment professional, or by the patient.

Further, the data from the sensor and/or an indication to initiate an alarm can be sent to a mobile device, desktop device, or other suitable device that can be accessed by the treatment professional or the patient, or other interested party (e.g., parent or guardian of the patient). Where an alarm indication is sent, the alarm can be initiated on a device such as a remote computing device accessible by the user or treatment professional. Such transfer of information can be accomplished in any suitable manner, for example, via Bluetooth or other wireless communication method.

Similar to the embodiment of FIG. 2, the embodiment of FIG. 3 can include a transmitter for transmitting compliance data. In this manner, less information needs to be stored on the storage case and therefore, the components of the circuit can cost less, among other benefits. For example, in some embodiments, the compliance component includes memory for storing compliance data. If the data is periodically transmitted to a remote device, the data can be removed from memory and therefore a smaller memory store may be used with the system.

In such embodiments, the compliance component includes a transmitter for transmitting compliance data and the memory stores the compliance data in a transmission queue until a device to receive the compliance data is within range to receive the data. Utilizing a queue can be beneficial, for example, by allowing the memory to hold compliance information that has been collected over a period of time and then transmit the data at a later time, such as at a check-up with the treatment professional or at the end of the treatment period in which the oral appliance is being used.

In some embodiments, the storage case can include a light source that can be used for various functions related to compliance. For example, a light source may be provided as an indicator that the patient is meeting a compliance goal. A light source may be provided as an indicator that the appliance has been placed correctly in the storage case such that compliance is being tracked. Further, a light source could be provided to aid an imaging sensor in sensing the appliance, as will be discussed in more detail with respect to the embodiment illustrated in FIG. 4 below.

When used to indicate compliance, in some implementations, the storage case can have one or more indicators, such as indicator 313, thereon that can be used to indicate compliance of other important information to the user and/or treatment professional. Any suitable indicator can be used that will alert a user or treatment professional to information that they should be aware of (e.g., status of compliance, etc.).

For example, light sources that illuminate to indicate whether the patient is in compliance or out of compliance with their wearing of the appliance. For example, the storage case may have a light that illuminates when the user is in compliance, such as the indicator 313 (e.g., a light source) shown on the exterior surface of the body of the storage case 312 of FIG. 3. Systems such as this could, alternatively, be designed to illuminate only when the patient is out of compliance.

Additionally, in some embodiments, the light source may be a display that displays text or one or more symbols that indicate compliance or non-compliance. Any suitable text or symbols could be used for such a purpose and the display utilized could be sized to accommodate such text and/or symbols.

Further, multiple lights could be used to indicate a level of compliance. For example, two lights, one green to indicate compliance and one red to indicate non-compliance, three lights with a green and red as above and a yellow to indicate they are nearing non-compliance, multiple lights where all illuminated indicates compliance and less lights indicates their level of non-compliance, etc. As the reader will understand, any suitable light arrangement could be used in the various embodiments of the present disclosure.

In another embodiment, an oral appliance compliance system includes a compliance component attached to a body of an oral appliance storage case wherein an oral appliance is to be placed when not in the mouth of a patient and the compliance component includes a power source and a sensor to indicate whether the patient is not storing the device for a period over a threshold period of time. In such an embodiment, the actual time that the appliance is not in the storage case is measured, which may be a better indicator of compliance by a patient in some implementations. One such embodiment is discussed with respect to FIG. 4.

Figure 4:
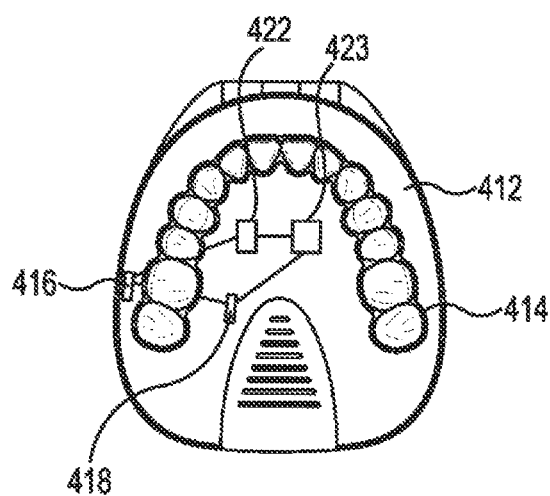
FIG. 4 illustrates an interior view of a storage case having an oral appliance therein according to a number of embodiments of the present disclosure.

FIG. 4 illustrates an interior view of a storage case having an oral appliance therein according to a number of embodiments of the present disclosure. In the embodiment of FIG. 4, the storage case includes a sensor that senses a characteristic of the oral appliance when the appliance is positioned within the storage case. The characteristic can be any characteristic of the oral appliance that can indicate its presence within the storage case. For example, in some embodiments, the characteristic can be the presence of a metallic material within the oral appliance. This could, for example, be accomplished through use of a magnetic sensor. Some or all of the components of the storage case in FIG. 4 may correspond to the components of FIG. 1A. For instance, the components of the storage case in FIG. 4 incorporate one or more portions of the extra-oral compliance indication system 1094, shown in FIG. 1A.

In some embodiments, the compliance component can be positioned within an oral appliance storage case where an oral appliance is to be placed when not in the mouth of a patient. The compliance component can include a power source and a sensor to indicate whether the patient is not storing the device for a period exceeding a threshold period of time.

In some embodiments, the compliance components can be added to a storage case that has already been fabricated. In this manner, compliance functionality can be added to any existing storage case for an oral appliance. This can be accomplished by, for example, placing the elements of the compliance system inside the storage case or using adhesive to affix one or more of the elements of the compliance system to the inside and/or outside surfaces of the body of the storage case.

For instance, in some embodiments, the sensor senses a characteristic of the oral appliance when the appliance is positioned within the storage case. Alternatively, the sensor can be designed to sense a characteristic of the oral appliance when the appliance is not positioned within the storage case (when the appliance is removed, it is no longer proximate to the sensor and, if the sensor is a proximity sensor, the sensor senses that the appliance is no longer proximate to the sensor). Examples of suitable sensors can be one or more of a proximity, density, mass, pressure, magnetic, and/or an imaging sensor, among other suitable types of sensors that can identify the physical presence of the appliance in the storage case.

In some embodiments, the characteristic of the appliance can be of an element provided on or within the appliance body. If the element is on the body or has a portion of the element that is in contact with the patient's tissue or fluids, it may be beneficial that the material be biocompatible. In some such embodiments, the oral appliance can include a biocompatible element that can be sensed by the sensor. Some magnetic materials would be examples of such biocompatible materials capable of being sensed by a sensor.

In embodiments where a storage case is utilized to accommodate the elements of the compliance system or where the power supply can sufficiently power such a functionality, compliance information can be pushed to a remote device by the transmitter of the compliance system. This may allow the compliance system to have little or no memory for storage and will allow the patient and/or treatment professional to immediately see the compliance data or analysis of compliance, or to allow such compliance analysis to take place within a close time period to when the data is being taken. This may be beneficial, for example, as the patient can rectify their behavior before the end of a treatment period and may be able to come into compliance with their treatment plan if their appliance wearing behavior is changed to increase the amount of time they are wearing the appliance.

As discussed above, in some implementations, one or more light sources may be part of the compliance system. A light source may, for example, be provided as an indicator that the appliance has been placed correctly in the storage case such that compliance is being tracked. Further, a light source could be provided to aid an imaging sensor in sensing the appliance.

In the embodiment shown in FIG. 4, a light source 416 is placed on one inside surface of the storage case 412 and an imaging sensor 418 is placed on another inside surface of the storage case, such that when an appliance 414 is placed into the storage case, the appliance can diminish or block the transmission of light from the light source that is received by the imaging sensor.

In this manner, the emitter (light source) and the detector (imaging sensor) can work together to identify whether the appliance is in the storage case. For example, if the imaging sensor indicates a certain voltage when the appliance is present and a different voltage when the appliance is not present, this data can be compared and a determination as to whether the appliance is present can be made.

Additionally, a system may just look at one voltage and compare it with a threshold voltage stored in memory of the device doing the analysis to determine whether the appliance is present or not. For example, a device may have a threshold reference voltage stored in memory 423 (e.g., provided in a processor/memory component 422) that indicates that the appliance is in the storage case.

The imaging sensor can provide a voltage level to the device doing the analysis and a determination can be made based upon whether the voltage level sent from the imaging sensor meets the threshold reference voltage. If the threshold reference voltage is met, then the appliance can be determined to be within the storage case. Alternatively, the analysis could be performed with a threshold reference voltage indicating that an appliance is not in the storage case. As the reader will understand, such a system could alternatively be used to show that the appliance is not in the storage case.

In other imaging sensor embodiments, the imaging sensor can be used to detect a feature on the dental appliance. For example, in some embodiments, the dental appliance can include a bar code or other identifier that indicates that it is a dental appliance as opposed to another object placed in the case. Any suitable identification marker can be used in such embodiments (e.g., one or more letters, numbers, shapes that can be identified by the system, or combination thereof). This could be accomplished by providing a known image on the appliance and comparing an image captured of the image with an image stored in memory on a computing device, for example.

Alternatively, a location on the appliance could be identified as being the location where an identifier will be present and if any identifier is located in an image captured of that location, then the appliance is deemed to be present. In this manner, analysis of the image captured is easy as it can just identify where an identifier is in the location or not.

The shape of the dental appliance may also change over time and could be used to determine whether the dental appliance is being used according to the treatment plan. For example, as a dental aligner is used to move teeth, it will change shape in a manner that may be predicted. In such an embodiment, the shape of the entire dental appliance or a portion that shows such deformation can be imaged and evaluated by the system. This can, for example, be accomplished by comparing an image of the appliance taken by the imaging sensor against one or more other images to determine if the appliance has deformed beyond a threshold change in shape.

Additionally, a pigment may be added to a portion of the dental appliance that, when interacting with saliva of the patient, changes color. In such embodiments, an imaging sensor can be used to capture the color of the pigment and determine whether the patient is being compliant based on comparing the captured image to colors stored in memory of a computing device that are indicative of dental appliances at certain periods of wear. In this manner, a pigment sample from an appliance that has been worn for 48 hours can be compared to the appliance of the patient, at a time when they should have worn their appliance for 48 hours, to see if the color of the pigments are within a threshold difference of being a match. If they are within the threshold of matching, then the patient is considered as being compliant in their wearing of the dental appliance.

This information can be used to determine the amount of time the appliance is in the storage case or out of the storage case, which can be used to infer how much time the appliance is in the patient's mouth and, thereby, compliance with the treatment plan. In some implementations, the emitter and detector can be positioned near each other and may even be on the same surface of the storage case.

In some embodiments, such as when used to provide illumination to an imaging sensor, the light source may not be visible to the human eye. This may be beneficial if the patient keeps their storage case near their bed so it does not disturb their sleep. For example, the light source and imaging sensor may operate in the UV or infrared wavelength ranges that are outside a human vision range.

Figure 5:
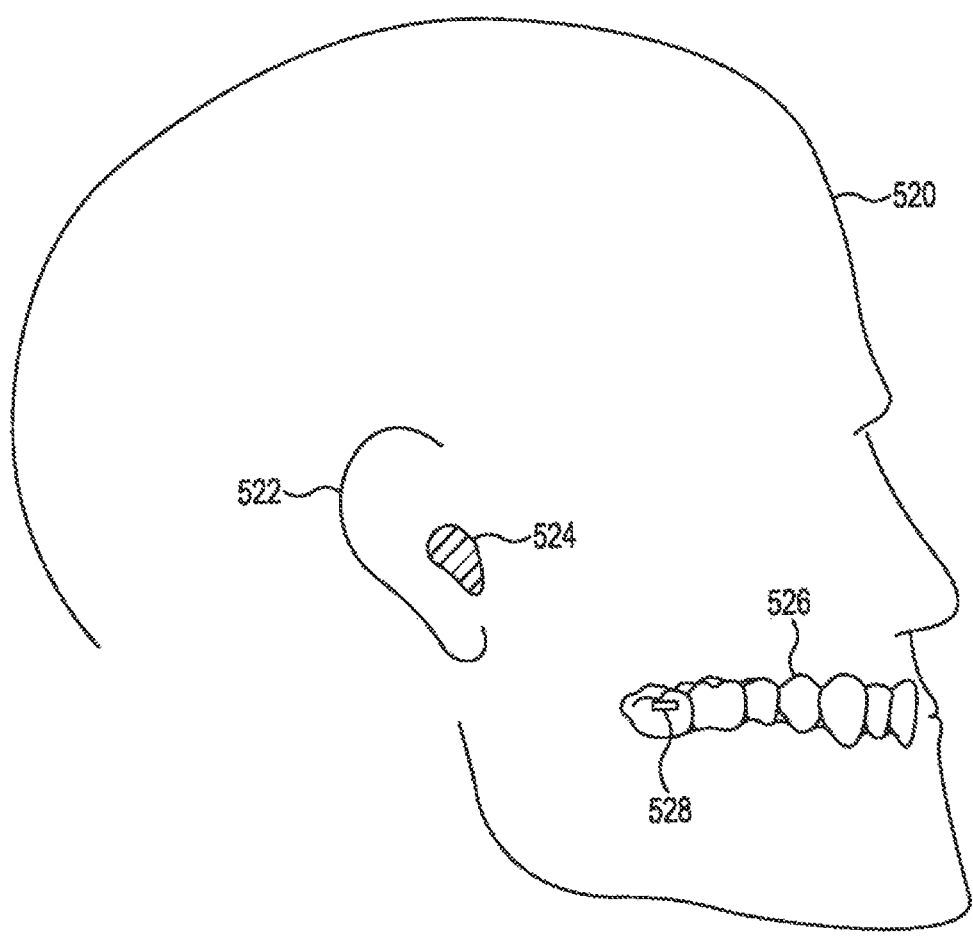
FIG. 5 illustrates a side view of the head of a patient with an oral appliance having a compliance indicator thereon positioned within the mouth of the patient and a remote sensor located in the ear of the patient according to a number of embodiments of the present disclosure.

FIG. 5 illustrates a side view of the head of a patient with an oral appliance having a compliance indicator thereon positioned within the mouth of the patient and a remote sensor located in the ear of the patient according to a number of embodiments of the present disclosure. For example, in some embodiments, an oral appliance compliance system includes an oral appliance and a compliance component attached to the body. In such embodiments, the compliance component can include a material that can be sensed by a remote sensor to indicate whether the oral appliance is in a patient's mouth.

In the embodiment of FIG. 5, the oral appliance 526 having a compliance component 528 thereon is positioned in the mouth of the patient. A remote sensing device 524 is placed within a threshold distance within which the compliance component 528 can be sensed. For example, in the embodiment illustrated in FIG. 5, the remote sensing device 524 is an ear piece that is positioned in the ear 522 of the patient. In other embodiments, the remote sensing device may be of a different form factor that may be positioned elsewhere on the head 520 or on another part of the patient's body or clothing, as will be described in more detail below.

The compliance component can be a passive component that is sensed when the remote sensor interacts with the compliance component. For example, some embodiments can have a passive detectable component (non-powered and/or non-transmitting) on or in the oral appliance and active detector components located outside the mouth of the patient. In such an embodiment, the active detector components can send out a signal that: can be received and a return signal sent by the passive detectable component (e.g., if the passive detectable component receives power from the active detector components) or be bounced off the passive detectable component, or the passive detectable component can be sensed (e.g., magnetic) by the active detector components.

For example, a small earpiece or other wearable or portable device, embedded with a Hall Effect sensor, can be worn throughout treatment. This device would detect when a magnet embedded in the aligner is detected. In such embodiments, the detection distance can be calibrated to the distance between where the device will be located and, for example, the 2nd molar of a particular patient (customized to a particular patient's needs), of an average patient (designed to be effective for most patients), or of a largest possible patient (to ensure the system will detect properly for all patients).

The device having the active detector components that is located outside the patient's mouth (extra-oral) can have various form factors. For example, the extra-oral wearable device can be a skin patch, wristband, watch, necklace, earing, accessory to a smart phone, etc. The passive detectable component could be or include a magnet, capacitor, or coil antenna. One benefit of such designs is that an extra-oral appliance may have more relaxed design constraints (e.g., size, biocompatibility, temperature and/or wetness of the environment), than an intra-oral appliance, which would only contain passive components.

As inferred by the possible form factors discussed above, the remote sensing device can be a portable device. This can be beneficial as the device can be removed from the body of the patient when the oral appliance is not being used, among other benefits. Further, as discussed with respect to the case in FIG. 3, in some embodiments, the portable device can include an indicator (e.g., one or more light sources, a display, etc.) that allows a user to see an indication of the level of compliance thereon.

The compliance component (passive detectable component) can be made from a variety of suitable materials depending on the conditions in which the compliance component is implemented. For example, in some embodiments, the compliance component material is a metallic material. In some implementations, the material is magnetic.

This can allow the compliance component to be non-power and detectable by a magnetic or electric field. This is accomplished because the magnetic or electric field will be slightly perturbed by the presence of a metallic object in proximity to the field and this perturbation can be sensed by a sensor.

In some embodiments, the compliance component includes a power source and the material that can be sensed is in the form of an antenna or a transmitter, wherein the transmitter transmits a signal that can be sensed by the remote sensor in the extra-oral appliance. For example, the material can be in the form of an antenna and the antenna transmits a signal that can be sensed by the remote sensor of the extra-oral device. The intra-oral device can be powered by a power source similar to the devices shown in FIGS. 1B and 2. In some embodiments, the intra-oral device can be energized by a signal from the extra-oral device received by the antenna of the intra-oral device and, once energized, can transmit a signal via the antenna to the extra-oral device.

In some embodiments, one extra-oral device can provide the power to the intra-oral device and another extra-oral device can receive the signal. For example, the signaling material of the intra-oral device can be in the form of an antenna and wherein the antenna transmits a signal that can be sensed by the remote sensor of a first device when the antenna is energized by a signal received by the antenna from a second remote device.

In some embodiments, an oral appliance compliance system can include a compliance component to be attached to a body of an oral appliance, wherein the compliance component includes a material that can be sensed by a remote sensor to indicate whether the oral appliance is in a patient's mouth. In this example embodiment, a remote sensing device can have the remote sensor therein to sense the presence of the material within a threshold distance from the remote sensor. In this manner, the sensing functionality can be performed by components that do not have to be located in the mouth of the patient. This can allow for a large form factor, components with more functionality or power, less biocompatibility considerations with respect to placing items in the patient's mouth, and other benefits.

In some such embodiments, the remote sensing device is a device that is wearable by the patient. For example, the remote sensing device is a device having the remote sensor therein selected from the group including: a piece of jewelry worn on the head of the patient (e.g., earring, ear piece, etc.), a piece of jewelry worn on the neck of the patient (e.g., necklace, etc.), a piece of jewelry worn on an appendage on the patient (e.g., watch, bracelet, anklet, etc.), a hair accessory, a pair of eyeglasses, or a device mounted to any such item.

The device may also be incorporated into an item that can be attached to the patient. For example a patch could include the remote sensing device and could be attached via an adhesive or other suitable type of attachment to attach to the body or the patient or to their clothing.

In some embodiments, an oral appliance compliance system includes an oral appliance to be placed into the mouth of a patient, a compliance component including a material that can be sensed by a remote sensor to indicate whether the oral appliance is in a patient's mouth, wherein the compliance component is attached to the oral appliance, and a remote sensing device having the remote sensor therein to sense the presence of the material within a threshold distance from the remote sensor. In this manner, compliance can be determined based on a proximity type of sensing and, as such, the sensing functionality can be located outside the mouth of the patient, in some implementations.

In embodiments where the compliance component is inside the mouth of the patient, the compliance component can be made from one or more biocompatible materials. Additionally or alternatively, the material that can be sensed is a biocompatible material. These types of embodiments can be beneficial, for example, if the compliance component is exposed to the patient's tissue or bodily fluids and as such may be review for compatibility by a government agency such as the US Food and Drug Administration.

The interaction between a compliance component and a remote sensor can be accomplished in a variety of suitable manners. For example, the interaction between the compliance component and the remote sensor can be accomplished via electromagnetic interaction. For instance radio frequency signals can be passed between an active or passive compliance component and a remote sensor.

In some implementations, the electromagnetic interaction between the compliance component and the remote sensor is via sensing of changes in an electromagnetic field. As discussed herein, this can be accomplished with a material that can be sensed when located within an electric or magnetic field that can be sensed by a sensing component. Examples of such material include magnetic materials and metallic materials, among others.

An embodiment such as those shown in FIGS. 1B-5 can generally be described as being an extra-oral dental appliance compliance indicator configured to be operational outside an oral cavity of a patient and configured to detect whether or not a dental appliance is being worn in the oral cavity of the patient. It should be noted that some embodiments of the present disclosure can be actuated intraorally as discussed herein.

Embodiments such as those shown in FIGS. 1B-5 also include an extra-oral sensor of the extra-oral dental appliance compliance indicator configured to sense whether a dental appliance is within the oral cavity of the patient and to provide a compliance signal to a processing device indicating whether the extra-oral sensor sensed that the dental appliance is within the oral cavity of the patient.

Figure 6:
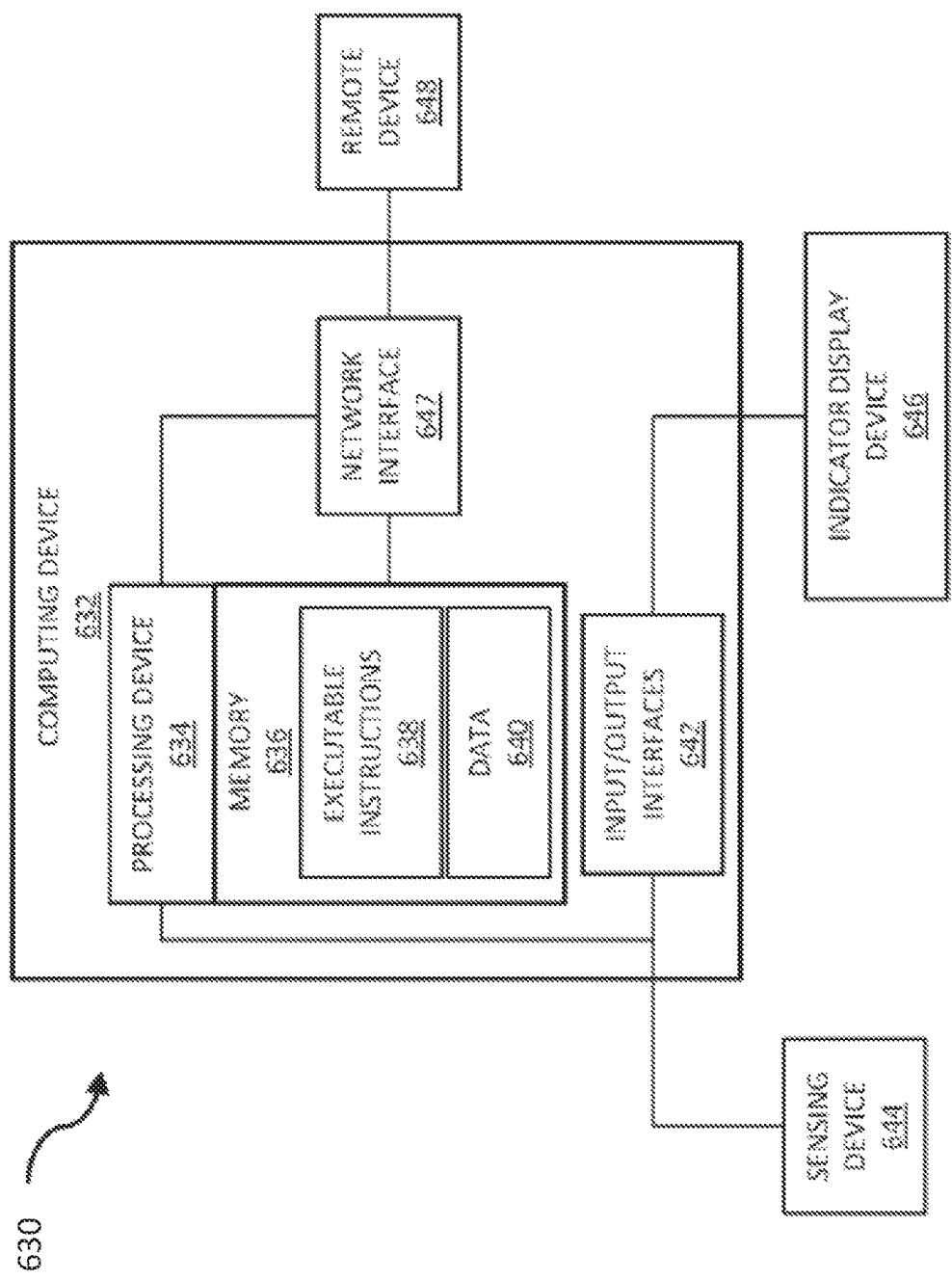
FIG. 6 illustrates a computing system for use in a number of embodiments of the present disclosure.

A processing device, such as device 634 discussed in FIG. 6, can be coupled (i.e., communicatively coupled) to the extra-oral sensor and the processing device configured to receive the compliance signal and to provide an indicator as to how much time the dental appliance has been worn. Such embodiments can also include a display device coupled to the processing device, the display device configured to display whether the patient is complying with a treatment plan based on how much time the dental appliance has been worn.

The extra-oral sensor can be several elements from FIGS. 1B-5. For example, the extra-oral sensor can be a power sensor configured to measure when an energy powered device on the appliance has lost energy such that an energy level of the energy powered device falls below an energy threshold indicative of the dental appliance being outside the oral cavity of the patient for more than a threshold period of time. In various embodiments, the extra-oral sensor is a power sensor that measures a power level of energy stored in an energy storage device. The embodiments of FIGS. 1B and 2 may have such power sensors as described above, in some implementations.

In various embodiments, the extra-oral sensor is incorporated into a case configured to store the dental appliance when the dental appliance is not in the oral cavity of the patient. The embodiments described with respect to FIGS. 3 and 4 may have such an extra-oral sensor, in some implementations.

As shown in the embodiment of FIG. 5, the extra-oral sensor can be a magnetic sensor configured to sense a magnetic field from a magnet on the dental appliance. For example, a Hall effect sensor or other suitable magnetic sensor could be utilized in various implementations.

In some implementations, the extra-oral dental appliance compliance indicator has the extra-oral sensor incorporated into a dental appliance packaging box and/or case.

FIG. 6 illustrates a computing system for use in a number of embodiments of the present disclosure. As shown in FIG. 6, computing device 632 of the computing system 630 can have a number of components coupled thereto. The computing device 632 can include a processor 634 and a memory 636. The memory 636 can have various types of information including executable instructions 638 and data 640, as discussed herein.

The processor 634 can execute instructions 638 that are stored on an internal or external non-transitory computer device readable medium (CRM). A non-transitory CRM, as used herein, can include volatile and/or non-volatile memory.

As discussed above with respect to FIG. 2, memory 636 and/or the processor 638 may be located on the computing device 632 or off of the computing device 632, in some embodiments. As such, as illustrated in the embodiment of FIG. 6, the computing device 632 can include a network interface 647.

Such an interface 647 can allow for processing on another networked computing device, can be used to obtain information about the patient (e.g., characteristics of the patient's mouth and/or treatment planning information) and/or can be used to obtain data and/or executable instructions for use with various embodiments provided herein. Also, as shown in FIG. 6, the network interface can allow for connection to one or more remote devices 648 (e.g., a mobile phone or other mobile or non-mobile computing device used by a patient, guardian, or treatment professional) to receive information from the compliance indication system regarding compliance of the patient in wearing the dental appliance.

In some embodiments, a computing device can be used to calculate time that the dental appliance has been worn and determine whether to initiate an indicator that the patient is either in compliance with their treatment plan regarding the amount of time the patient should be wearing the dental appliance or is not in compliance. This can be accomplished, for example, by executing instructions, via a processing device (e.g., computer processor), to compare an amount of time the patient has worn the dental appliance over a period of time to a treatment plan time threshold for that period of time. For example, if the time the patient has worn their dental appliance is calculated at 100 hours for a one week period of time and the time threshold for that time period is 98 hours, the patient can be considered as being in compliance with the treatment plan, which includes the time threshold for one or more periods of time over the time that the treatment plan is being performed.

As illustrated in the embodiment of FIG. 6, the computing device 632 can include one or more input and/or output interfaces 642. Such interfaces 642 can be used to connect the computing device 632 with one or more input and/or output devices 644, 646.

For example, in the embodiment illustrated in FIG. 6, the input and/or output devices can include a sensing device 644 and an indicator display device 646. As discussed herein, the sensing device can provide compliance information to the computing device 632, for example, by sensing when the dental appliance is within the oral cavity of the patient or is outside the oral cavity of the patient. The indicator display device 646 can be any suitable device for providing a patient, guardian, or treatment professional with an indication that the patient is in compliance or out of compliance with the treatment plan.

Such connectivity with input and output devices and network connections can allow for the input and/or output of data and/or instructions among other types of information. Some embodiments may be distributed among various computing devices within one or more networks, and such systems as illustrated in FIG. 6 can be beneficial in allowing for the capture, calculation, and/or analysis of information discussed herein.

The processor 634, can be in communication with the data storage device (e.g., memory 636), which has the data 640 stored therein. The processor 634, in association with the memory 636, can store and/or utilize data 640 and/or execute instructions 638 for compliance indication.

In various embodiments, the processing device 634 coupled to the memory 636 can cause the computing device 632 to perform the method comprising receiving, via a processing device, one or more compliance signals generated from an extra-oral sensor of an extra-oral dental appliance compliance indicator configured to be operational outside an oral cavity of a patient and configured to sense whether a dental appliance is within the oral cavity of the patient, calculating a time that the dental appliance has been in the oral cavity of the patient based on the received one or more compliance signals, comparing the calculated time to a treatment plan time threshold to determine if the patient is complying with a treatment plan, and initiating an indicator that indicates to the patient whether or not they are complying with the treatment plan based on the comparison of the calculated time to the treatment plan time threshold.

Such analysis can be accomplished one or more times for a treatment plan. For example, if a treatment plan has 30 stages, it would be possible to have different dental appliance compliance periods for each stage or possibly more, if desired.

Figure 7:
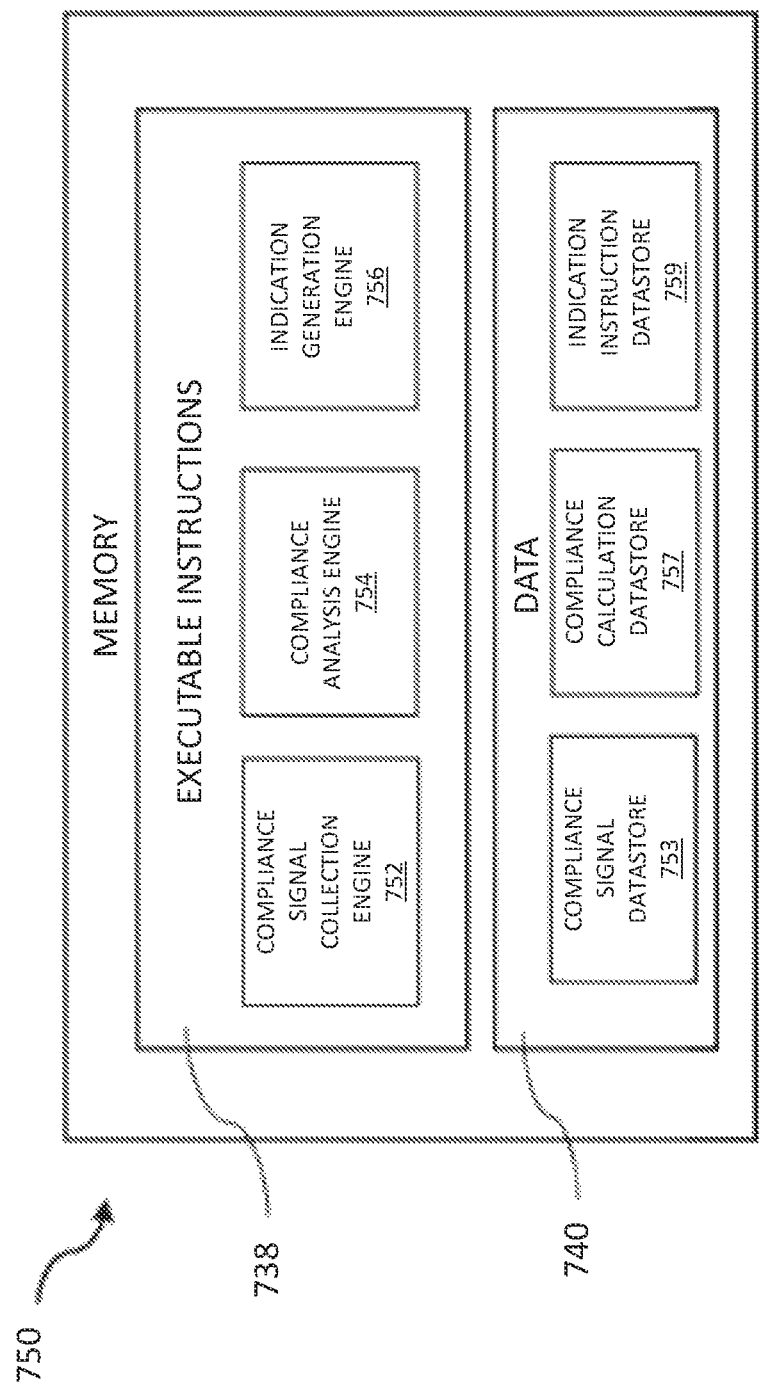
FIG. 7 illustrates a memory for use in a number of embodiments of the present disclosure.

FIG. 7 illustrates a memory for use in a number of embodiments of the present disclosure. Memory 750 may be, for example, memory 636 previously described in connection with FIG. 6.

The memory 750 may have various types of information including executable instructions 738 and data 740, as discussed herein. Additionally, the memory 750 may include one or more engines and datastores. A computing system can be implemented as an engine, as part of an engine, or through multiple engines.

The compliance signal collection engine 752 may include one or more automated agents configured to gather compliance signals from an extra-oral sensor and/or the compliance signal datastore 753. The compliance signal collection engine can use this information to calculate a time that a patient has been wearing the dental appliance. Compliance signals can, for example, be a time stamp (e.g., the time that the dental appliance was taken out of the oral cavity of the patient), an elapsed time quantity (e.g., the time period that the dental appliance was out of the oral cavity of the patient). When a time stamp is utilized, the processing device can execute instructions to determine the time period between a time stamp when the dental appliance was taken out and a time stamp when the dental appliance was placed back into the oral cavity. This information can then be used to determine the one or more time periods that the patient had the dental appliance positioned within their oral cavity.

The compliance analysis engine 754 may include one or more automated agents configured to determine whether the patient is in compliance with their treatment plan based on the time calculations made by the compliance signal collection engine 752 and one or more treatment plan thresholds stored, for example, in the compliance calculation datastore 757.

The indication generation engine 756 may include one or more automated agents configured to determine whether to initiate an indication be generated to inform the patient, guardian, or treatment professional that the patient is in compliance or out of compliance based on the determination made by the compliance analysis engine. The indication generation engine 756 can use data from the indication instruction datastore 759 to determine, for example, who to send an indication, what contact information to use to communicate the indication, how often to send an indication (every day/week/month, every time a non-compliance event occurs or wait until several events occur until sending an indication, etc.).

Through use of such executable instructions and data, embodiments of the present disclosure can determine whether a patient in compliance with a treatment plan and provide an indication to one or more parties to alert them of the status of the patient. Such embodiments can be beneficial in improving compliance and in tracking compliance more accurately so that, for example, changes in a patient's routine can be made before issues arise from the patient not following the treatment plan.

Figure 8:
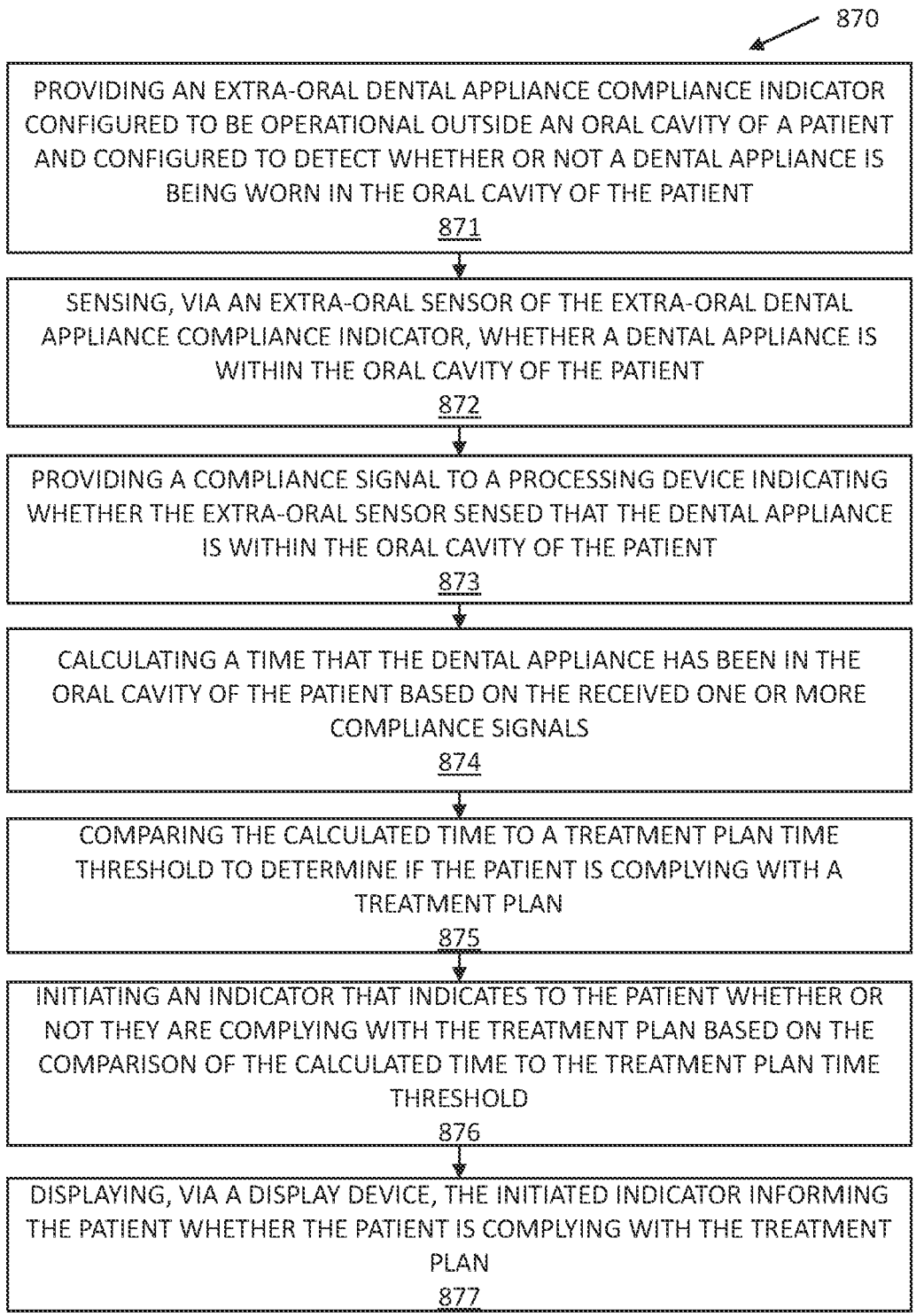
FIG. 8 illustrates a method for compliance indication, according to some implementations of the present disclosure.

FIG. 8 illustrates a flowchart of a method 870 for compliance indication, according to some implementations of the present disclosure. The method 870 may include more or less operations than those explicitly shown in FIG. 8. Some or all of the operations of the method 870 may be executed by the computing system 630 shown in FIG. 6 and/or the structures shown in FIG. 1A.

In the embodiment of FIG. 8, the compliance indication method 870 illustrated includes providing an extra-oral dental appliance compliance indicator configured to be operational outside an oral cavity of a patient and configured to detect whether or not a dental appliance is being worn in the oral cavity of the patient, at 871. The method further includes, at 872, sensing, via an extra-oral sensor of the extra-oral dental appliance compliance indicator, whether a dental appliance is within the oral cavity of the patient. At 873, a compliance signal is provided to a processing device indicating whether the extra-oral sensor sensed that the dental appliance is within the oral cavity of the patient.

The time that the dental appliance has been in the oral cavity of the patient based on the received one or more compliance signals is calculated at 874. The calculated time is compared, at 875, to a treatment plan time threshold to determine if the patient is complying with a treatment plan.

An indicator that indicates to the patient whether or not they are complying with the treatment plan based on the comparison of the calculated time to the treatment plan time threshold is initiated, at 876. And, at 877, the initiated indicator informing the patient whether the patient is complying with the treatment plan, can be displayed, via a display device. Through use of such an embodiment, compliance can be determined, and the information can be presented to a patient, guardian, or treatment profession to allow them to better assess the compliance of the patient among other benefits.

In some embodiments, the method can also include measuring, via a power sensor, when an energy powered device on the appliance has lost energy such that an energy level of the energy powered device falls below an energy threshold indicative of the dental appliance being outside the oral cavity of the patient for more than a threshold period of time. As discussed with respect to FIG. 1B, the power sensor can, for example, be configured to close a circuit only when the dental appliance is outside the oral cavity of the patient. In such an embodiment, the circuit will only be in operation when the dental appliance is not being worn by the patient.

Figure 9:
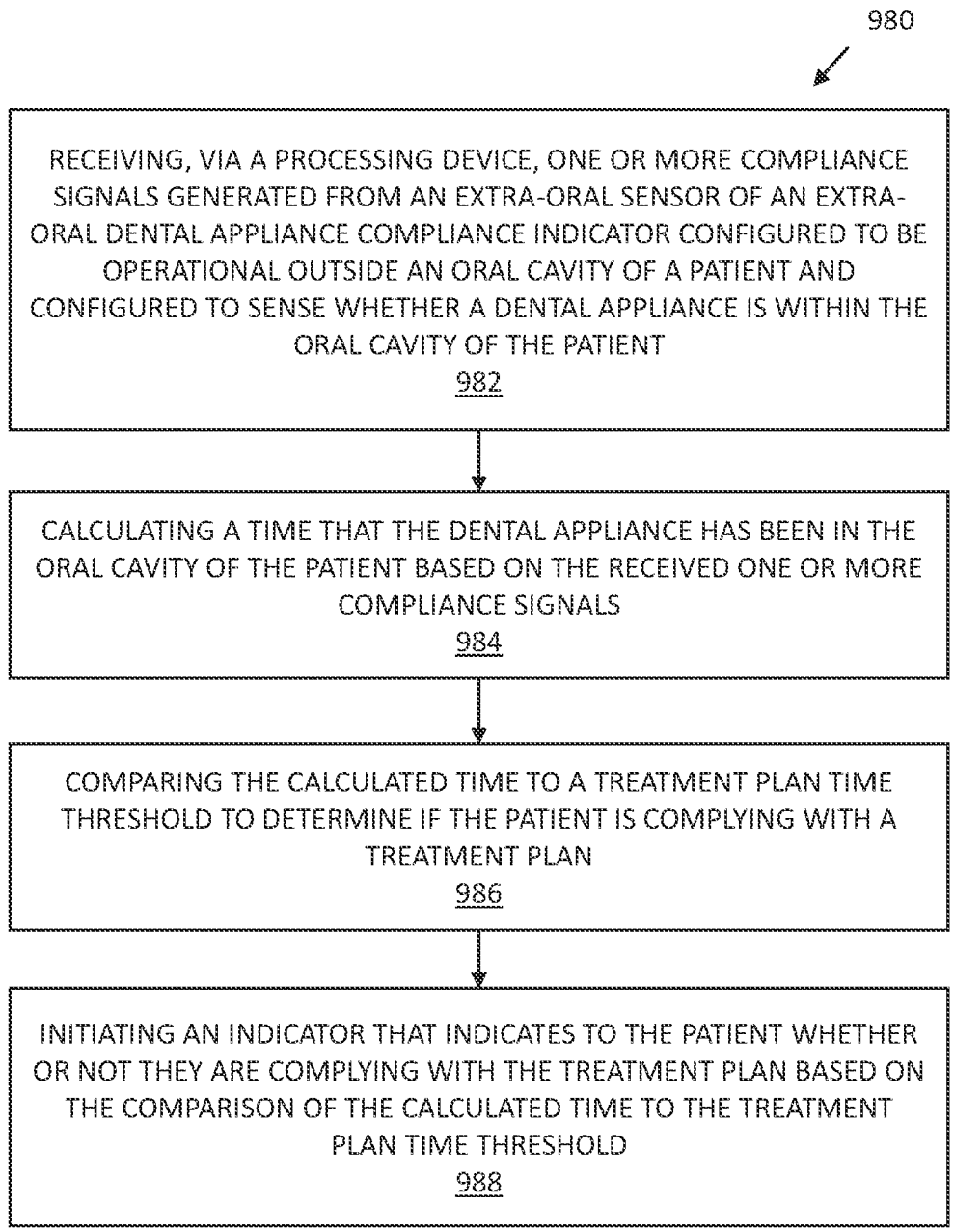
FIG. 9 illustrates another method for compliance indication, according to some implementations of the present disclosure.

A method embodiment as shown in FIG. 9 can also include a calculation process for calculating how much time the dental appliance has been worn based on the compliance signal received from the extra-oral sensor. This can be accomplished by the processes described herein and can be handled via executing instructions via the processing device, such as the device shown at 634 of FIG. 6.

Methods can also include determining an amount of time the dental appliance has been out of the oral cavity over a period of time to determine how much time the dental appliance is being worn. For example, a period of time could be a stage of a treatment plan, a day, a week, a month, during the entire treatment plan, or other suitable period of time. The amount of time the dental appliance has been out of the oral cavity can be continuous time (e.g., an uninterrupted span of 14 hours) or cumulative time over a period (e.g. 7 hours on day 1, 10 hours on day 2, 14 hours on day 3, 4 hours on day 4, and 15 hours on day 5 for a total cumulative time over the five day period of 50 hours).

In some embodiments, the processing device is configured to have a real time clock circuit that is used with the compliance signal to determine a time period that the dental device has been outside the oral cavity of the patient. The extra-oral sensor can also include or alternatively include a clock circuit configured to count the amount of time that the dental appliance is outside the oral cavity of the patient. As discussed herein, such timing circuits can be beneficial in providing accuracy to the timing measurements used in the determination of compliance.

FIG. 9 illustrates another method for compliance indication, according to some implementations of the present disclosure. As with the method of FIG. 8, the method 980 may include more or less operations than those explicitly shown in FIG. 9. Some or all of the operations of the method 980 may be executed by the computing system 630 and/or other structures shown in FIG. 9.

In the embodiment of FIG. 9, the compliance indication method 980 includes receiving, via a processing device, one or more compliance signals generated from an extra-oral sensor of an extra-oral dental appliance compliance indicator configured to be operational outside an oral cavity of a patient and configured to sense whether a dental appliance is within the oral cavity of the patient, at 982.

A time that the dental appliance has been in the oral cavity of the patient based on the received one or more compliance signals is calculated, at 984. The calculated time is compared, at 986, to a treatment plan time threshold to determine if the patient is complying with a treatment plan. An indicator that indicates to the patient whether or not they are complying with the treatment plan based on the comparison of the calculated time to the treatment plan time threshold is initiated, at 988.

Similar to the embodiment of FIG. 8, in embodiments such as that shown in FIG. 9, the method can also include displaying, via a display device, the initiated indicator informing the patient whether the patient is complying with the treatment plan. The displaying of such information can, for example, by accomplished through use of a light emitting diode display device, presentation of a voltage value on a display device, or an indication presented on a software application on a display of a mobile device, among other suitable display mechanisms. Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

Figure 10:
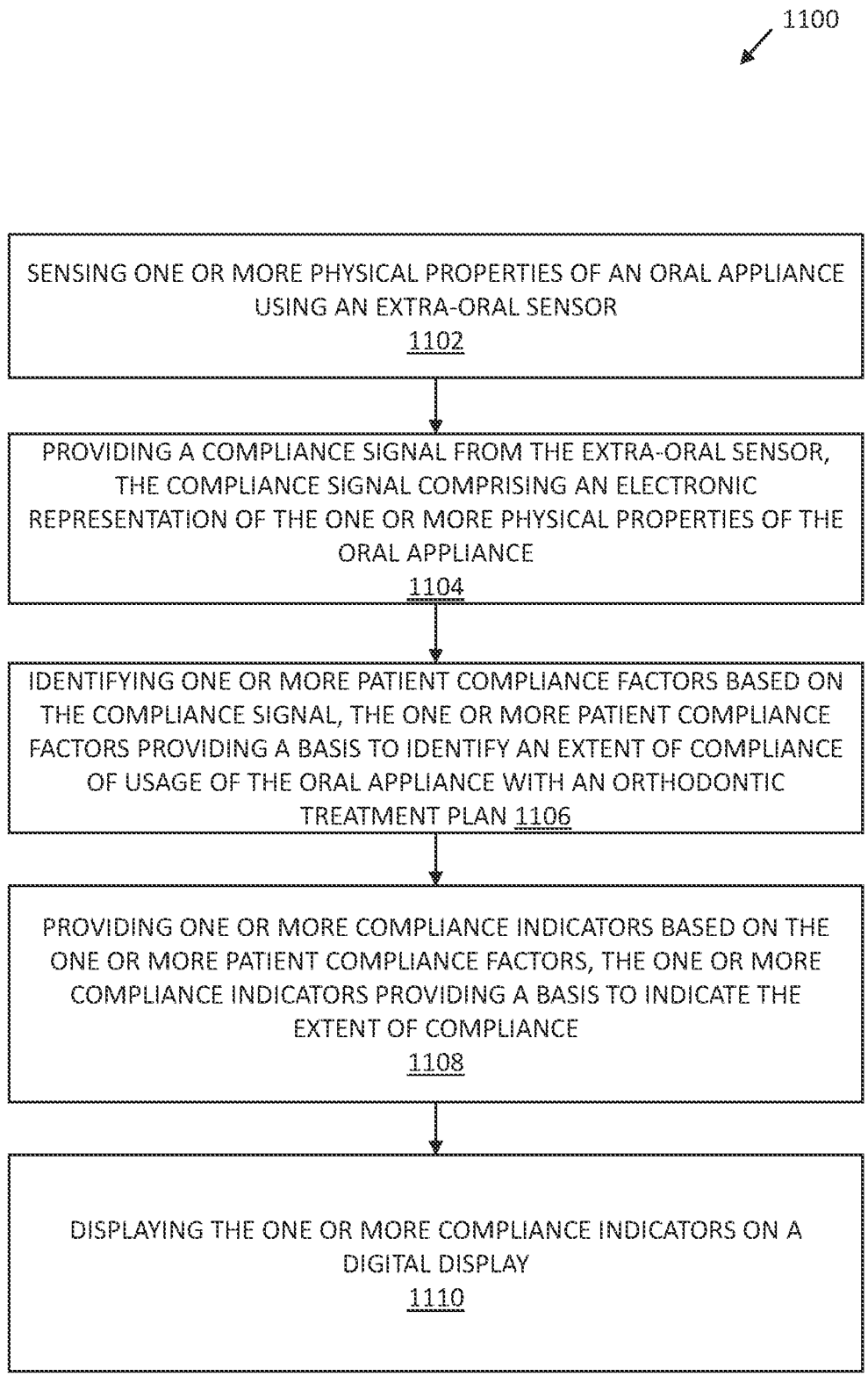
FIG. 10 shows a flowchart of a method of providing compliance indicators, according to some implementations of the present disclosure.

FIG. 10 shows a flowchart of a method 1100 of providing compliance indicators, according to some implementations. As with other methods herein, the method 1100 may include more or less operations than those explicitly shown in FIG. 10. Some or all of the operations of the method 1100 may be executed by any of the structures described herein.

At an operation 1102, one or more properties of an oral appliance may be sensed using an extra-oral sensor. The extra-oral sensor may comprise a discharge circuit configured to discharge power from a power source through a power draining element when the oral appliance is at a specified orientation relative to an oral cavity. The extra-oral sensor may comprise a magnetic sensor configured to detect when the oral appliance is at a specified orientation relative to an oral cavity. In some implementations, the extra-oral sensor comprises a Hall effect sensor incorporated in an extra-oral cavity of a patient associated with the oral appliance. The extra-oral sensor may include a metallic sensor configured to detect a metallic portion of the oral appliance. Such a metallic sensor may be incorporated into a case of the oral appliance. Further, the extra-oral sensor may comprise a biosensor configured to detect presence or absence of one or more biological chemicals on the oral appliance. In some implementations, the extra-oral sensor comprises a light source sensor configured to determine whether the oral appliance blocks a light source. The light source sensor may be incorporated into a case of the oral appliance. In various implementations, the extra-oral sensor comprises one or more image sensors configured to capture an image of the oral appliance.

At an operation 1104, a compliance signal may be provided from the extra-oral sensor. The compliance signal may comprise an electronic representation of the one or more physical properties. In some implementations, the electronic representation of the one or more physical properties of the oral appliance represents the one or more physical properties of the oral appliance. The electronic representation of the one or more physical properties of the oral appliance may represent whether or not the oral appliance is in a case associated with the oral appliance. In some implementations, the electronic representation of the one or more physical properties of the oral appliance represents a location of the oral appliance.

At an operation 1106, one or more patient compliance factors may be identified. The one or more patient compliance factors may provide a basis to identify an extent of compliance of usage of the oral appliance with an orthodontic treatment plan. At an operation 1108, one or more compliance indicators may be provided. The one or more compliance indicators may provide a basis to indicate the extent of compliance. At an operation 1110, the one or more compliance indicators may be displayed on a digital display.

It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A storage case for an oral appliance, the storage case comprising:
   a body having a shape and size for storing the oral appliance; and
   a compliance indicator system including:
   a sensor configured to sense one or more physical properties of the oral appliance and to provide a compliance signal that is associated with a time that the oral appliance is within the storage case;
   one or more processors;
   memory coupled to the one or more processors, the memory comprising computer-program instructions that, when executed by the one or more processors, cause the compliance indicator system to:
   identify one or more patient compliance factors based on the compliance signal, the one or more patient compliance factors providing a basis to determine an extent of compliance of usage of the oral appliance with an orthodontic treatment plan specific to a patient;
   determine the extent of compliance of the patient based on the orthodontic treatment plan specific to the patient and the one or more patient compliance factors; and
   output the extent of compliance of the patient for one or more stages of the orthodontic treatment plan.

2. The storage case of claim 1, wherein the compliance signal indicates whether the oral appliance was in the storage case over a threshold period of time.

3. The storage case of claim 1, wherein the compliance indicator system further comprises a power supply.

4. The storage case of claim 3, wherein compliance indicator system includes a switch mechanism configured to turn the power supply on or off.

5. The storage case of claim 3, wherein the compliance indicator system is configured to determine compliance based on a power level of the power supply compared to a pretreatment power level or based on a predetermined threshold power level.

6. The storage case of claim 1, wherein the compliance indicator system further comprises a light source configured to generate light, wherein the sensor is an imaging sensor configured to sense diminished or blockage of light generated by the light source.

7. The storage case of claim 1, wherein the compliance indicator system includes a clock circuit configured to measure the time that the oral appliance is within the storage case.

8. The storage case of claim 1, wherein the compliance indicator system further comprises a transmitter to transmit compliance data to a remote device.

9. The storage case of claim 1, further comprising a near field communication component that is configured to transfer energy from a device that comes within the range of a near field antenna of the near field communication component to a power supply of the storage case.

10. The storage case of claim 1, wherein the sensor is configured to be activated by a latch that keeps the storage case closed.

11. The storage case of claim 1, wherein the compliance indicator system further comprises an alarm that is configured to activate when the time that the oral appliance is within the storage case is greater than a threshold time period.

12. The storage case of claim 1, wherein the computer-program instructions is configured to identify the one or more patient compliance factors based on the compliance signal that is specific to one or more of a plurality of different stages of the treatment plan.

13. The storage case of claim 1, wherein the computer-program instructions is configured to output the extent of compliance by indicating to the patient whether or not the patient is complying with the treatment plan.

14. The storage case of claim 1, wherein the treatment plan requires the patient to wear the oral appliance for a specified circumstance.

15. The storage case of claim 1, wherein the treatment plan specifies an amount of time per day for each stage that the oral appliance is to be worn.

16. A method of measuring an extent of compliance of usage of an oral appliance, the method comprising:
   generating a compliance signal from a sensor of a storage case for the oral appliance, the sensor configured to sense one or more physical properties of the oral appliance associated with a time that the oral appliance is within the storage case;
   wherein the sensor is part of a compliance indicator system integrated into the storage case, the compliance indicator system comprising:
   one or more processors;
   memory coupled to the one or more processors, the memory comprising computer-program instructions that, when executed by the one or more processors, cause the compliance indicator system to:
   identify one or more patient compliance factors based on the compliance signal, the one or more patient compliance factors providing a basis to determine an extent of compliance of usage of the oral appliance with an orthodontic treatment plan specific to a patient;
   determining the extent of compliance of the patient based on the orthodontic treatment plan specific to the patient and the one or more patient compliance factors; and
   outputting the extent of compliance of the patient for one or more stages of the treatment plan.

17. The method of claim 16, wherein the one or more patient compliance factors is determined based at least in part on a power level of the power supply compared to a pretreatment power level or based on a predetermined threshold power level.

18. The method of claim 16, wherein outputting further comprises transmitting the extent of compliance from the storage case to a remote device.

19. The method of claim 16, wherein the computer-program instructions is configured to identify one or more patient compliance factors specific to one or more of a plurality of different stages of the treatment plan.

20. The method of claim 16, wherein outputting the extent of compliance for one or more stages of the treatment plan comprises outputting an indicator that indicates to the patient whether or not the patient is complying with the treatment plan.

21. The method of claim 16, wherein determining the extent of compliance comprises determining the extent of compliance in a remote computing device.

22. The method of claim 16, wherein the treatment plan requires the patient to wear the oral appliance for a specified circumstance.

23. The method of claim 16, wherein the treatment plan specifies an amount of time per day for each stage that the oral appliance is to be worn.

* * * * *